(12) United States Patent
Langell et al.

(10) Patent No.: US 11,324,387 B2
(45) Date of Patent: May 10, 2022

(54) MEDICAL BORESCOPES AND RELATED TIP ASSEMBLIES

(71) Applicant: Xenocor, Inc., Salt Lake City, UT (US)

(72) Inventors: John Langell, Salt Lake Ciry, UT (US); Lane Brooks, Highland, UT (US)

(73) Assignee: Xenocor, Inc., Salt Lake City, UT (US)

( * ) Notice: Subject to any disclaimer, the term of this patent is extended or adjusted under 35 U.S.C. 154(b) by 0 days.

(21) Appl. No.: 16/921,882

(22) Filed: Jul. 6, 2020

(65) Prior Publication Data
US 2020/0329951 A1 Oct. 22, 2020

Related U.S. Application Data

(63) Continuation of application No. 16/460,822, filed on Jul. 2, 2019, now Pat. No. 10,702,128, which is a
(Continued)

(51) Int. Cl.
*H04N 7/18* (2006.01)
*A61B 1/00* (2006.01)
(Continued)

(52) U.S. Cl.
CPC ...... *A61B 1/00022* (2013.01); *A61B 1/00006* (2013.01); *A61B 1/00009* (2013.01); *A61B 1/00011* (2013.01); *A61B 1/00057* (2013.01); *A61B 1/00059* (2013.01); *A61B 1/00062* (2013.01); *A61B 1/00103* (2013.01); *A61B 1/00105* (2013.01); *A61B 1/00108* (2013.01); *A61B 1/00121* (2013.01);
(Continued)

(58) Field of Classification Search
None
See application file for complete search history.

(56) References Cited

U.S. PATENT DOCUMENTS

| 4,919,112 A | 4/1990 | Siegmund |
|---|---|---|
| 5,188,092 A | 2/1993 | White |

(Continued)

FOREIGN PATENT DOCUMENTS

| CN | 101116626 | 2/2008 |
|---|---|---|
| CN | 102245076 | 11/2011 |

(Continued)

OTHER PUBLICATIONS

Japanese Patent Application No. 2016-576076, Office Action dated Mar. 20, 2019 (3 pgs).
(Continued)

*Primary Examiner* — Eileen M Adams
(74) *Attorney, Agent, or Firm* — Matthew D. Thayne; Thayne and Davis LLC

(57) ABSTRACT

Medical borescopes and related methods. In some embodiments, a medical borescope may comprise a handle and a tube extending from the handle. The tube may be partially, or wholly, defined by an at least substantially non-conductive material, such as a suitable plastic, ceramic, or other non-metallic material. The borescope may further comprise a tip assembly positioned at a distal end of the tube, which may comprise an image sensor configured to take images through the distal end of the tube.

20 Claims, 17 Drawing Sheets

Related U.S. Application Data continuation of application No. 15/953,221, filed on Apr. 13, 2018, now Pat. No. 10,335,015, which is a continuation of application No. 14/958,728, filed on Dec. 3, 2015, now Pat. No. 9,943,214, which is a continuation-in-part of application No. 14/790,977, filed on Jul. 2, 2015, now abandoned.

(60) Provisional application No. 62/020,389, filed on Jul. 2, 2014.

(51) Int. Cl.
| | |
|---|---|
| *H04N 5/232* | (2006.01) |
| *A61B 5/01* | (2006.01) |
| *G02B 23/24* | (2006.01) |
| *A61B 1/045* | (2006.01) |
| *A61B 5/00* | (2006.01) |
| *H04N 5/225* | (2006.01) |

(52) U.S. Cl.
CPC .......... *A61B 1/00195* (2013.01); *A61B 1/045* (2013.01); *A61B 5/01* (2013.01); *A61B 5/7246* (2013.01); *G02B 23/2476* (2013.01); *H04N 5/23209* (2013.01); *H04N 7/183* (2013.01); *H04N 2005/2255* (2013.01)

(56) References Cited

U.S. PATENT DOCUMENTS

| | | | |
|---|---|---|---|
| 5,416,634 | A | 5/1995 | Ning |
| 5,701,155 | A | 12/1997 | Wood et al. |
| 5,892,630 | A | 4/1999 | Broome |
| 6,110,103 | A | 8/2000 | Donofrio |
| 6,796,939 | B1 | 9/2004 | Hirata et al. |
| 7,033,317 | B2 | 4/2006 | Pruitt |
| 8,038,602 | B2 | 10/2011 | Gill et al. |
| 8,398,540 | B2 | 3/2013 | Hassidov et al. |
| 8,460,182 | B2 | 6/2013 | Ouyang et al. |
| 8,764,632 | B2 | 7/2014 | Kezirian et al. |
| 8,827,899 | B2 | 9/2014 | Farr et al. |
| 8,858,425 | B2 | 10/2014 | Farr et al. |
| 9,033,870 | B2 | 5/2015 | Farr et al. |
| 10,335,015 | B2 | 7/2019 | Langell et al. |
| 2002/0188173 | A1 | 12/2002 | Kobayashi |
| 2005/0080342 | A1 | 4/2005 | Gilreath et al. |
| 2005/0228294 | A1* | 10/2005 | Yamaki .................. G16H 40/67 600/478 |
| 2006/0038988 | A1 | 2/2006 | Thermos |
| 2006/0293556 | A1 | 12/2006 | Garner |
| 2008/0051634 | A1 | 2/2008 | Yamashita |
| 2008/0249355 | A1 | 10/2008 | Birnkrant et al. |
| 2009/0088215 | A1 | 2/2009 | Giraldo et al. |
| 2009/0076329 | A1 | 3/2009 | Su |
| 2009/0082630 | A1 | 3/2009 | Tulley |
| 2009/0312601 | A1 | 12/2009 | Shigemori |
| 2009/0318758 | A1* | 12/2009 | Farr ........................ A61B 90/53 600/112 |
| 2010/0198009 | A1 | 8/2010 | Farr et al. |
| 2011/0009694 | A1 | 1/2011 | Schultz et al. |
| 2011/0087256 | A1 | 4/2011 | Wiener et al. |
| 2012/0191091 | A1 | 7/2012 | Allen |
| 2012/0289858 | A1 | 11/2012 | Ouyang et al. |
| 2013/0096378 | A1 | 4/2013 | Alexander et al. |
| 2013/0096382 | A1 | 4/2013 | Alexander et al. |
| 2013/0204085 | A1 | 8/2013 | Alexander et al. |
| 2013/0278739 | A1* | 10/2013 | Tanaka .................. A61B 1/0002 348/72 |
| 2014/0320617 | A1* | 10/2014 | Parks ................... A61B 1/00181 348/65 |
| 2015/0011830 | A1 | 1/2015 | Hunter et al. |
| 2015/0080755 | A1 | 3/2015 | Jackson |
| 2015/0173593 | A1* | 6/2015 | Han ........................ A61B 1/051 600/109 |
| 2015/0216400 | A1 | 8/2015 | Iida et al. |
| 2015/0317816 | A1 | 11/2015 | Bendall |
| 2016/0000301 | A1 | 1/2016 | Langell et al. |
| 2017/0027650 | A1* | 2/2017 | Merck ................ A61B 1/00188 |

FOREIGN PATENT DOCUMENTS

| | | |
|---|---|---|
| CN | 102647936 | 8/2012 |
| CN | 103400090 | 11/2013 |
| CN | 103533881 | 1/2014 |
| WO | 2009134634 | 11/2009 |
| WO | 2010066787 | 6/2010 |
| WO | 2014157796 | 10/2014 |

OTHER PUBLICATIONS

Translation of Japanese Patent Application No. 2016-576076, Office Action dated Mar. 20, 2019, (4 pgs).
U.S. Appl. No. 14/790,977, Office Action dated Aug. 7, 2017, (9 pgs).
International Search Report for PCT/US2016/064846, dated Feb. 16, 2017, (2 pgs).
Written Opinion for PCT/US2016/064846, dated Feb. 16, 2017, (6 pgs).
International Search Report for PCT/US15/39113, dated Oct. 7, 2015, (2 pgs).
Written Opinion for PCT/US15/39113, dated Oct. 7, 2015, (6 pgs).
Extended European Search Report for EP16871676.9, dated Jun. 19, 2019 (9 pgs).
U.S. Appl. No. 14/790,977, Office Action dated Oct. 29, 2018, (14 pgs).
Machine Translation of CN102245076A (7 pgs).
Machine Translation of CN102647936A (28 pgs).
Machine Translation of CN103533881A (10 pgs).
Machine Translation of CN103400090A (7 pgs).
Machine Translation of CN101116626A (55 pgs).

* cited by examiner

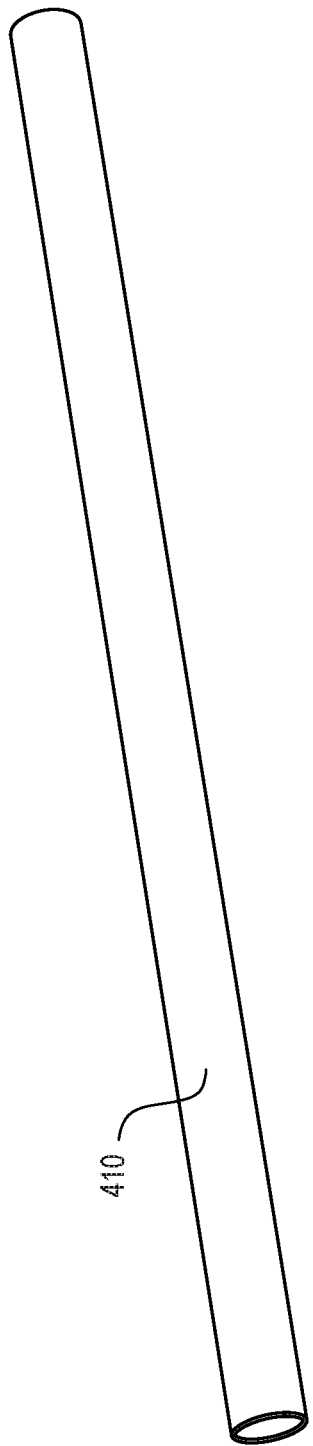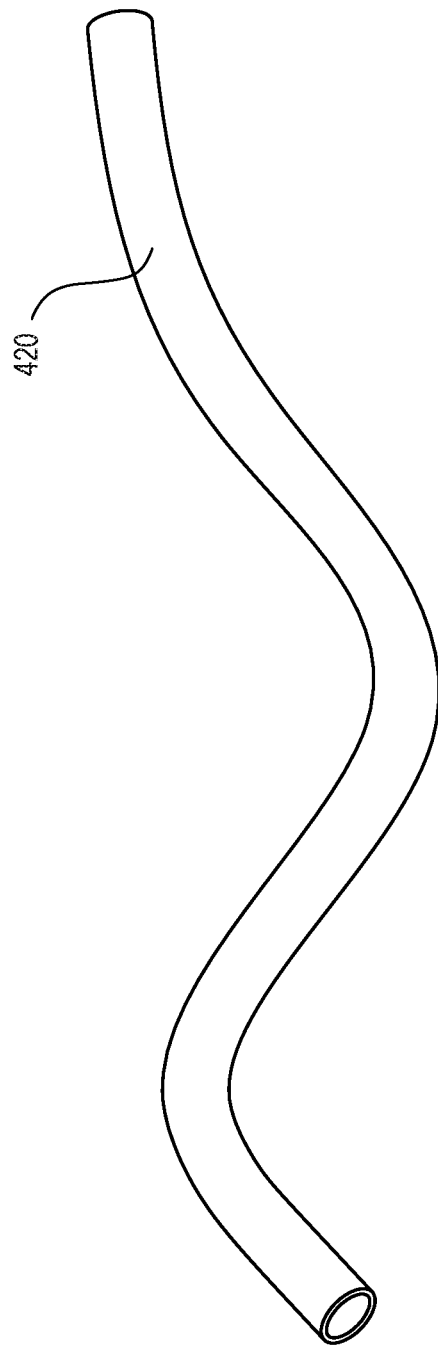

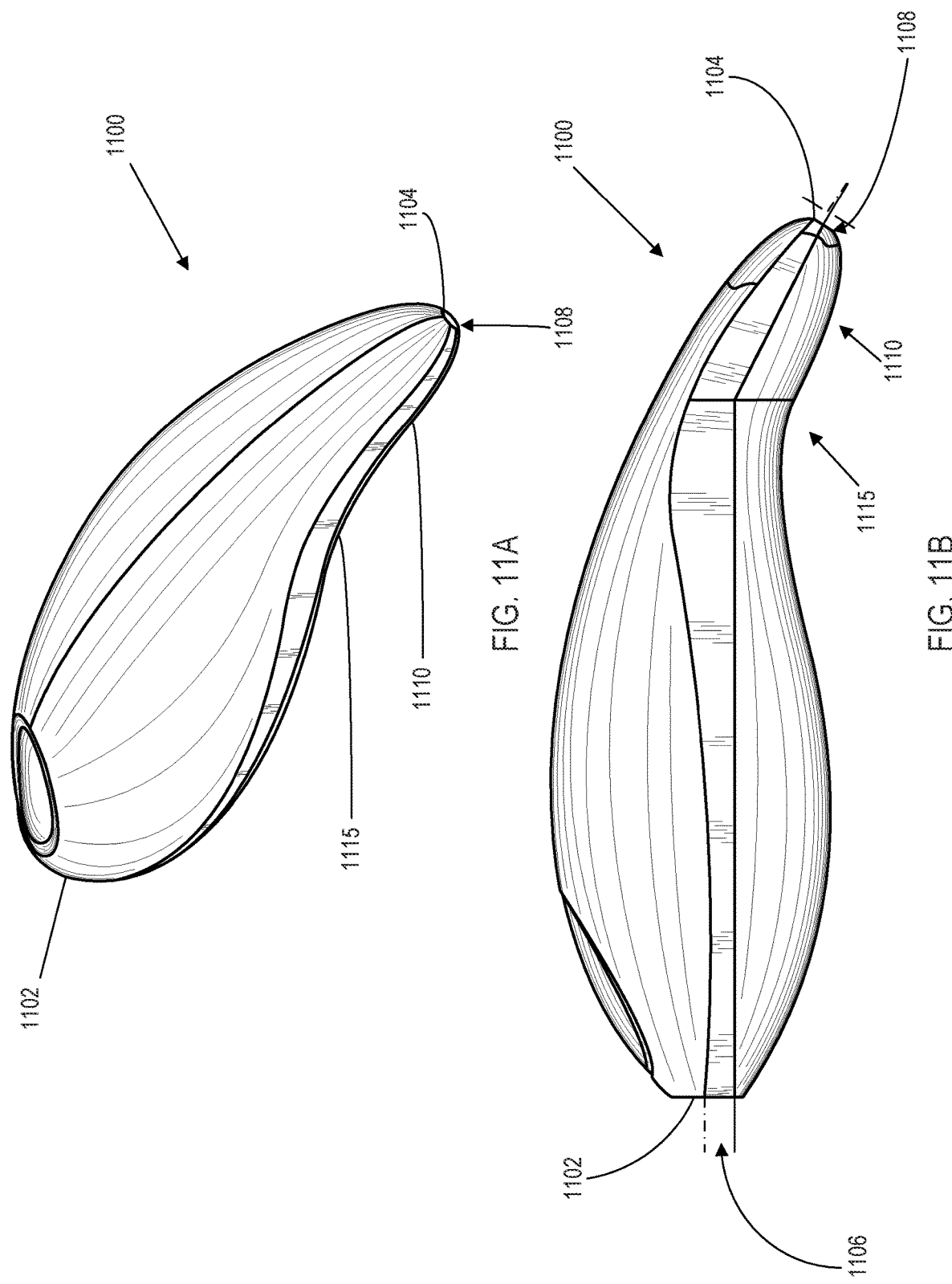

MEDICAL BORESCOPES AND RELATED TIP ASSEMBLIES

CROSS-REFERENCE TO RELATED APPLICATIONS

This application is a continuation of co-pending application Ser. No. 16/460,822 titled "MEDICAL BORESCOPES AND RELATED TIP ASSEMBLIES," which was filed Jul. 2, 2019 and is a continuation of U.S. Pat. No. 10,335,015, which was filed on Apr. 13, 2018 and titled "MEDICAL BORESCOPES AND RELATED METHODS AND SYSTEMS," which is a continuation of U.S. Pat. No. 9,943,214, which was filed on Dec. 3, 2015 and also titled "MEDICAL BORESCOPES AND RELATED METHODS AND SYSTEMS," which is a continuation-in-part of application Ser. No. 14/790,977, filed on Jul. 2, 2015 and titled "BORESCOPES AND RELATED METHODS AND SYSTEMS," which claims the benefit under 35 U.S.C. § 119(e) of U.S. Provisional Patent Application No. 62/020,389, which was filed Jul. 2, 2014 and titled "PORTABLE SCOPE FOR MEDICAL PROCEDURES." Each of the aforementioned applications is hereby incorporated herein by reference in its entirety.

TECHNICAL FIELD

Embodiments of this invention relate to borescoping technology, which may include, for example, laparoscopy, endoscopy, other related medical borescoping, and other industrial applications, such as engine, turbine, or building inspections.

BACKGROUND

Borescope technology has been applied to the medical field for many years. For example, laparoscopy and endoscopy both involve a medical professional inserting a borescope into a patient. The borescope allows the medical practitioner to view the patient's internal organs without having to expose the organs to the open air through surgery.

In a conventional laparoscopic system, a laparoscope, comprising a rod lens tube and a handle body, connects to a processing stack, which is used to process image data received from a laparoscope. The rod lens tube is the portion of the laparoscope that is inserted into a patient's abdominal cavity. A high intensity light is introduced into the lens and illuminates the tissue. Light reflected off the surfaces of the tissue is transmitted back up the rod lens into a camera, which captures an image that is transmitted through a wire to image processing equipment in the equipment stack.

As described above conventional laparoscopic systems suffer from several shortcomings. For example, laparoscopic systems require large stacks of equipment to generate the light and process the video image. The light is typically a high intensity xenon light source that is delivered to the laparoscope through a fiber optic cable. The fiber optic cable is fragile and gets in the way of the medical practitioners. In addition, the high intensity light sources can be extremely hot, even burning patients or starting patient covering drapes on fire if improperly monitored. In addition, the light source can vary in color or intensity from one setup to the next or over time, thereby requiring frequent white balancing. Additionally, the rod lenses are fragile, which limits their use in certain conditions and/or necessitates costly repairs or replacement. Indeed, an entire secondary industry has developed that focuses on repairing broken rod lens tubes.

SUMMARY

Embodiments disclosed herein may comprise systems, methods, and apparatus configured to provide medical professionals with a highly portable medical borescope system (e.g., laparoscope system) that eliminates the need for an external light source or large video imaging processing equipment. Although preferred embodiments may be most suitable for use in the medical field, it is contemplated that a variety of other fields may benefit from this disclosure. For example, various embodiments disclosed herein may have industrial applications, such as inspection and/or maintenance of aircraft engines, other engines and/or turbines, building inspections, tank inspection, surveillance, forensics, and the like. Because many such applications, like many medical applications, involve visual inspection of areas that can be messy and/or involve remote access points, the portability and/or disposability features disclosed herein may be particularly useful in connection with a variety of fields and applications, both medical and non-medical in nature.

Some embodiments disclosed herein may provide a laparoscope body that is disposable or suitable for single use or a limited number of uses (e.g., 10 uses). In some such embodiments, the system may be configured to enforce disposability. For example, some embodiments may be configured to track usage data, such as, for example, a duration of operation and/or a number of times the borescope has been turned on. In some such embodiments, the system may be configured to disable or alter an operational and/or control parameter of the borescope in response to determining that an operational parameter or threshold has been exceeded.

In some embodiments, the dongle may be used to query the borescope for certain data that may be stored on the borescope, such as, for example, model identification data or calibration data. The dongle may then be configured to change certain operational or control parameters based upon the data received from the borescope. For example, the dongle may be used to use the data received from the borescope to adjust the display characteristics of the images generated by the borescope so that the clinician is able to view images of the same or similar quality, irrespective of the variation in lens and/or LED outputs that may be received from different borescopes. In this manner, a single dongle may also be used with a variety of different borescopes.

In some embodiments, the dongle and/or borescope may also, or alternatively, be configured to obtain and store usage data that may be used to provide data to governmental authorities, for example, similar to the use of a "black box" in the context of the airline industry. One or more sensors may be located in the tip, or elsewhere, of the borescope. Such sensors may be used to receive various data, such as temperatures, pressures, velocities, images, orientations, etc., which may be used to recreate certain aspects of a medical procedure. For example, in some embodiments, such data may be tracked throughout a medical procedure, or at intermittent points throughout a medical procedure. In other embodiments, certain events, particularly unexpected events, may trigger gathering of such data.

In some embodiments, a clock and/or timer may be provided on the dongle and/or borescope. This clock/timer may be used to correlate certain usage data with a date stamp. In this manner, certain aspects of a medical procedure may be correlated with usage data so that certain aspects of the procedure may be recreated and traced to the particular time or times during which they occurred. In embodiments in which the borescope contains model identification data, this data may be stored and linked to the usage data so that it can be determined which borescope used in conjunction with a particular dongle was associated with a particular set of usage data.

The system may also include a portable image processing dongle in communication with the laparoscope. The dongle outputs the video image to a display. The dongle can include common display connectors such as, for example, HDMI, USB, or Lightning™ connectors for attaching a non-proprietary display or connecting a proprietary display through a universal connector.

In some embodiments, the mobility and/or disposability of the laparoscope may be achieved by placing an LED and image sensor within the body of the laparoscope (i.e., within the portion of the laparoscope that is placed in the sterile field of the patient). For example, some embodiments comprise a medical borescope tube that has a first tube end and a second tube end. The first tube end can be distal from a handle body and the second tube end can be in communication with the handle body. A light source and an image sensor may be disposed at the first tube end. A power source may be in communication with the light source and the image sensor. A data link may connect the image sensor to an image processor. The image processor may be disposed within a dongle that is connected to the handle body through a flexible wire.

In at least one alternative embodiment, instead of communicating to a dongle, a mobile computing device, such as a tablet or mobile phone, may be in communication with the handle body, such as via wired cables and/or wireless communication links, for example. As such, the mobile computing device can process the image data and provide a display to view the processed data. The mobile computing device may also provide additional general computing functionality relating to sharing medical data and analyzing image data.

As an additional example, some implementations may comprise methods for processing image data received from an image sensor disposed within a tip of a medical borescope device. The method can comprise serializing image data received from an image sensor or otherwise receiving and/or processing image data from an image sensor, which image sensor may be disposed at a first end of a medical borescope tube. The method can further comprise transmitting the image data (in some implementations, serialized image data) down the medical borescope tube to a second end of the medical borescope tube. Additionally, the method can comprise deserializing or otherwise processing and/or receiving the image data at an image processor, which may be located within a dongle that is in communication with the image sensor. The method can also comprise interpolating color from the image data, correcting color saturation, filtering out noise, gamma encoding, and/or converting the image data from RGB to YUV using the image processor.

In some embodiments, the image processor (e.g., in the dongle) includes a white balancing module. The white balancing module may set the white balance based on the color spectrum of the LED in the tip of the borescope. Thus, the image processing may be pre-calibrated during the manufacturing stage, thereby avoiding the need of the user to adjust the white balance with each use.

In a preferred embodiment, the borescope may include a fixed lens that is pre-focused at the desired depth of field. The lens may be placed at the distal end of the borescope just distal to the sensor at a fixed distance to create a fixed lens. The fixed lens and image sensor at the distal end may be pre-focused, thereby eliminating the need for the medical practitioner to focus the lens. The fixed lens, pre-focused, pre-calibrated white balance allows a medical practitioner to plug in the borescope to a monitor and receive high quality imaging with minimal technical assistance or adjustments.

In an example of a medical borescope device according to some embodiments, the device may comprise a tube comprising a first tube end and a second tube end opposite from the first tube end. A handle body may be coupled with the tube. A light source, such as a light emitting diode, may be positioned adjacent to the first tube end and configured to generate light at the first tube end. The device may further comprise an image sensor positioned adjacent to the first tube end and a power source, such as a battery, that may be configured to provide power to at least one of the light source and the image sensor. In some embodiments, the battery or other power source may be used to provide power to the light source, the image sensor, and/or any other components of the device requiring power.

A data communication link may be coupled with the image sensor. The device may further comprise a dongle comprising an image processor configured to receive image data from the image sensor. This may allow the device to be coupled with a standard display of a portable computing device, thereby reducing costs and increasing the mobility/portability of the imaging system. In some embodiments, the dongle may comprise common, universal, and/or non-customized display connectors such as HDMI or USB, for example, such that a common, non-customized, non-proprietary display, such as a display from a mobile general-purpose computing device may be used to display images from the device. Thus, in some embodiments, the dongle may be configured to be coupled with a mobile general-purpose computing device to allow a display of such a device to be used to display images from the device. In some embodiments, the power source may be part of the dongle.

In some embodiments, the first tube end is distal from the handle body, and the second tube end is coupled to the handle body. In some embodiments, the dongle may be coupled or coupleable to the handle body. Thus, in some embodiments, particularly in disposable embodiments, the dongle may be configured to be removed from the device and attached to a new device after disposal of the original device, or at least a portion of the original device. In other embodiments, however, the dongle may be disposable along with the rest of the device, or at least along with the rest of the disposable portion of the device.

Some embodiments may further comprise a flexible wire connector for coupling the dongle to the handle body. Alternatively, the dongle may be electrically coupled directly to the handle body, or another part of the device, without an intervening wire. For example, in some embodiments, the dongle may be plugged into the handle body, or another part of the device. Alternatively, the dongle may be wirelessly coupled with the device.

In some embodiments, the device may comprise a tip assembly that may comprise a printed circuit board. In some such embodiments, the image sensor may be positioned on or otherwise coupled with the printed circuit board. In some embodiments, the light source may be spaced apart from the circuit board. Thus, some such embodiments may comprise a spacing mount configured to space the light source apart from the circuit board. In some embodiments, the spacing mount itself may comprise a printed circuit board. Alternatively, the spacing mount may solely be configured so as to space the light source from the circuit board and the light source may be coupled by other means to another circuit board.

In some embodiments, at least a portion of the medical borescope device may be disposable. In some such embodiments, the medical borescope device may be configured to limit at least one of a duration and a number of uses of the medical borescope device to a preconfigured value. This may be accomplished, for example, by recording at least one of the duration and the number of uses on a flash memory component or another such non-volatile memory component located within the medical borescope device. In some embodiments, this memory component may be located within a tip assembly of the device, which tip assembly may be detachable from the rest of the device. In some such embodiments, the memory component may be positioned on a printed circuit board located within the tip assembly.

In an example of a medical borescope system according to some embodiments, the system may comprise a medical borescope. The medical borescope may comprise a handle body coupled with the tube and a light source positioned adjacent to the first tube end and configured to generate light at the first tube end. The borescope may further comprise an image sensor positioned adjacent to the first tube end and a data communication link coupled with the image sensor.

The system may further comprise a mobile general-purpose computing device, such as a mobile phone, tablet, or laptop computer having a visual display coupled to the medical borescope. The mobile general-purpose computing device may comprise an image processor configured to receive image data from the image sensor of the borescope. The visual display of the mobile general-purpose computing device may be configured to display information received from the image processor.

In an example of a method for processing image data received from an image sensor positioned within a medical borescope device according to some implementations, the method may comprise receiving image data from an image sensor positioned within a medical borescope device. The image data may be sent to an image processor, which image processor may be located within either a dongle or a mobile general-purpose computing device coupled with the medical borescope device. The image data may then be processed using the image processor and the resulting processed image data may be transmitted from the image processor to a visual display.

Some implementations may further comprise disposing of the medical borescope device, or disposing of at least a portion of the device. Thus, as mentioned above, some embodiments may be specifically configured to be used once, or be used a predetermined number of times and/or for a predetermined time duration. In some such embodiments, a second medical borescope device may be coupled with either the dongle or the mobile general-purpose computing device after disposal of the first device, or at least a portion of the first device. The original medical borescope device and the second medical borescope device may, in some implementations and embodiments, both be configured to limit at least one of a duration and a number of uses of the medical borescope device to a preconfigured value. Thus, in some such embodiments and implementations, a memory component may be configured to store cycle on/offs associated with the device and/or usage time and the device may be configured to transmit a command upon detecting a threshold number of uses and/or usage time to cause the device to become disabled, or to otherwise limit use of the device.

In another example of a medical borescope system according to some embodiments, the system may comprise a medical borescope comprising a tube comprising a first tube end and a second tube end opposite from the first tube end; a light source positioned adjacent to the first tube end and configured to generate light at the first tube end; and an image sensor positioned adjacent to the first tube end. The system may further comprise a data communication link coupled with the image sensor and a dongle comprising an image processor configured to receive image data from the image sensor. The dongle may be removably coupleable with the medical borescope such that the dongle can be coupled with a plurality of distinct medical borescopes. The dongle may further be configured to at least one of receive and detect borescope-specific parameter data, such as calibration data associated with the medical borescope and/or at least one of a serial number and a model number associated with the medical borescope. Preferably, the borescope-specific parameter data is stored in the medical borescope and comprises data unique to the medical borescope.

In some embodiments, at least a portion of the medical borescope device is disposable. In some such embodiments, the medical borescope device may be configured to determine at least one of a duration and a number of uses of the medical borescope device to enforce disposability of the at least a portion of the medical borescope device. In some such embodiments, the medical borescope device may be configured to determine at least one of the duration and the number of uses of the medical borescope device by using the dongle to detect at least one of the duration and the number of uses. In some such embodiments, the dongle may be configured to limit at least one of the duration and the number of uses of the medical borescope device to a threshold value by, upon detecting a use of the medical borescope device beyond the threshold value, at least one of disabling the medical borescope device, providing an audible warning, providing a visible warning, and transmitting a warning signal.

In another example of a method for medical imaging according to some implementations, the method may comprise removably coupling a dongle with a first medical borescope device. The first medical borescope device may be disposable, and may comprise borescope data stored on a memory component of the first medical borescope device. The method may further comprise receiving at the dongle from the first medical borescope device at least some of the borescope data. In some implementations, all of the borescope data may be transmitted to the dongle.

The method may further comprise adjusting an operational parameter of the first medical borescope device using the dongle and the at least some of the borescope data. Image data may also be received at the dongle from an image sensor positioned within the first medical borescope device and may be processed at the dongle using an image processor positioned within the dongle. The first medical borescope device may then be disposed of so that the dongle may be coupled with a second medical borescope device. The second medical borescope device may also comprise borescope data stored on a memory component of the second medical borescope device. The borescope data of the second medical borescope device may be distinct from the borescope data of the first medical borescope device.

In some such implementations, the two medical borescope devices can be distinguished from one another using their respective borescope data. Thus, in some implementations, the borescope data of the first medical borescope device may comprise information unique to the first medical borescope device, and the borescope data of the second medical borescope device comprises information unique to the second medical borescope device. The borescope data of the first medical borescope device may comprise, for example, model identification data for the first medical borescope, and the borescope data of the second medical borescope device may comprise model identification data for the second medical borescope. Alternatively, or additionally, the borescope data of the first medical borescope device may comprise calibration data for the first medical borescope, and the borescope data of the second medical borescope device may comprise calibration data for the second medical borescope.

Some implementations may further comprise recording usage data associated with the second medical borescope device. In some such implementations, the dongle may be used to process the usage data to determine whether the second medical borescope device has exceeded a threshold use parameter and, upon detecting a use of the second medical borescope device in violation of the threshold use parameter, the dongle may be used to at least one of disable the second medical borescope device, providing an audible warning, providing a visible warning, and transmitting a warning signal.

In a particular example of a method for obtaining and storing usage data from a medical borescope according to some implementations, the method may comprise obtaining a medical borescope comprising a tube comprising a first tube end and a second tube end opposite from the first tube end; a light source positioned adjacent to the first tube end and configured to generate light at the first tube end; and an image sensor positioned adjacent to the first tube end. The method may further comprise coupling a dongle to the medical borescope, the dongle comprising an image processor configured to receive image data from the image sensor. Usage data from the medical borescope during a medical procedure may be stored on the dongle, after which the dongle may be removed from the medical borescope. The usage data may then be accessed, such as transferred to another computer or system, to obtain information regarding usage of the medical borescope during the medical procedure, and/or the data may be stored to a database for potential later access.

In some implementations, the dongle may comprise a memory component. In some such implementations, the step of storing usage data may comprise storing the usage data on the memory component. In other implementations, the medical borescope may comprise a memory component. In some such implementations, the step of storing usage data may comprise storing the usage data on the memory component.

The usage data may comprise, for example, one or more of a duration of the medical procedure, an image associated with an unexpected event during the medical procedure, a time stamp associated with the medical procedure, a temperature measurement associated with the medical procedure, and a power cycle counter associated with the medical borescope.

Some implementations may further comprise initiating at least one of a clock and a counter upon initiation of a medical procedure with the medical borescope. Some such implementations may comprise correlating at least one-time stamp from the at least one of a clock and a counter with sensory data, such as, for example, image data, temperature data, velocity data, orientation data, and the like, that is obtained during the medical procedure.

Some implementations may further comprise correlating the usage data with model identification data associated with the medical borescope. In some implementations, the model identification data may comprise at least one of a serial number and a model number associated with the medical borescope.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter. In addition, the features, structures, steps, or characteristics disclosed herein in connection with one embodiment may be combined in any suitable manner in one or more alternative embodiments.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4B depicts an embodiment of an interchangeable borescope tube;

FIG. 4C depicts another embodiment of an interchangeable borescope tube;

FIG. 11A is a perspective view of a handle body for a borescope system according to an alternative embodiment;

FIG. 11B is a side elevation view of the handle body of FIG. 11A;

DETAILED DESCRIPTION OF THE PREFERRED EMBODIMENTS

Embodiments disclosed herein may comprise systems, methods, and apparatus configured to provide medical professionals with a highly portable medical borescope system (e.g., laparoscope or endoscope system) that may eliminate the need for an external light source or bulky and/or customized video imaging processing equipment. Some embodiments may comprise a laparoscope body that is disposable or suitable for single use or a limited number of uses (e.g., 10 uses). In some embodiments, the system may further comprise a portable image processing dongle in communication with the laparoscope. The dongle may output the video image to a display. The dongle can include one or more common display connectors such as HDMI, USB, and/or Lightning connectors for attaching a non-proprietary display or connecting a proprietary display through a universal connector.

The mobility and/or disposability of the laparoscope is achieved by placing an LED and image sensor within the body of the laparoscope (i.e., within the portion of the laparoscope that is placed in the sterile field of the patient).

Accordingly, implementations disclosed herein may allow medical professionals to utilize medical borescope technologies in a variety of different locations, including in the field. Additionally, some implementations may allow a medical professional to use a single medical borescope system to efficiently perform a variety of different medical borescope procedures. For example, a medical professional can use the same medical borescope system to perform both endoscopic procedures and laparoscopic procedures. As such, some implementations may provide significant benefits in third world countries and countries with otherwise deficient medical services by providing a low-cost and highly transportable medical borescope system.

Additionally, some implementations can be easily incorporated into a wide variety of different medical systems. For example, many conventional surgical suites comprise highly integrated systems that only communicate with medical devices from a single manufacturer or group of manufacturers. In contrast, some implementations disclosed herein may provide for communication to a single dongle device, which performs the necessary image processing and provides output ports that communicate through a variety of different universal protocols, such as HDMI, VGA, USB, DISPLAY PORT, MINI DISPLAY PORT, and other common protocols. Accordingly, some implementations may allow a medical borescope system to communicate with a variety of conventional devices such as a standard high definition television, a tablet computer, a desktop computer, and or any other display device that comprises commonly used communication ports.

Figure 1:
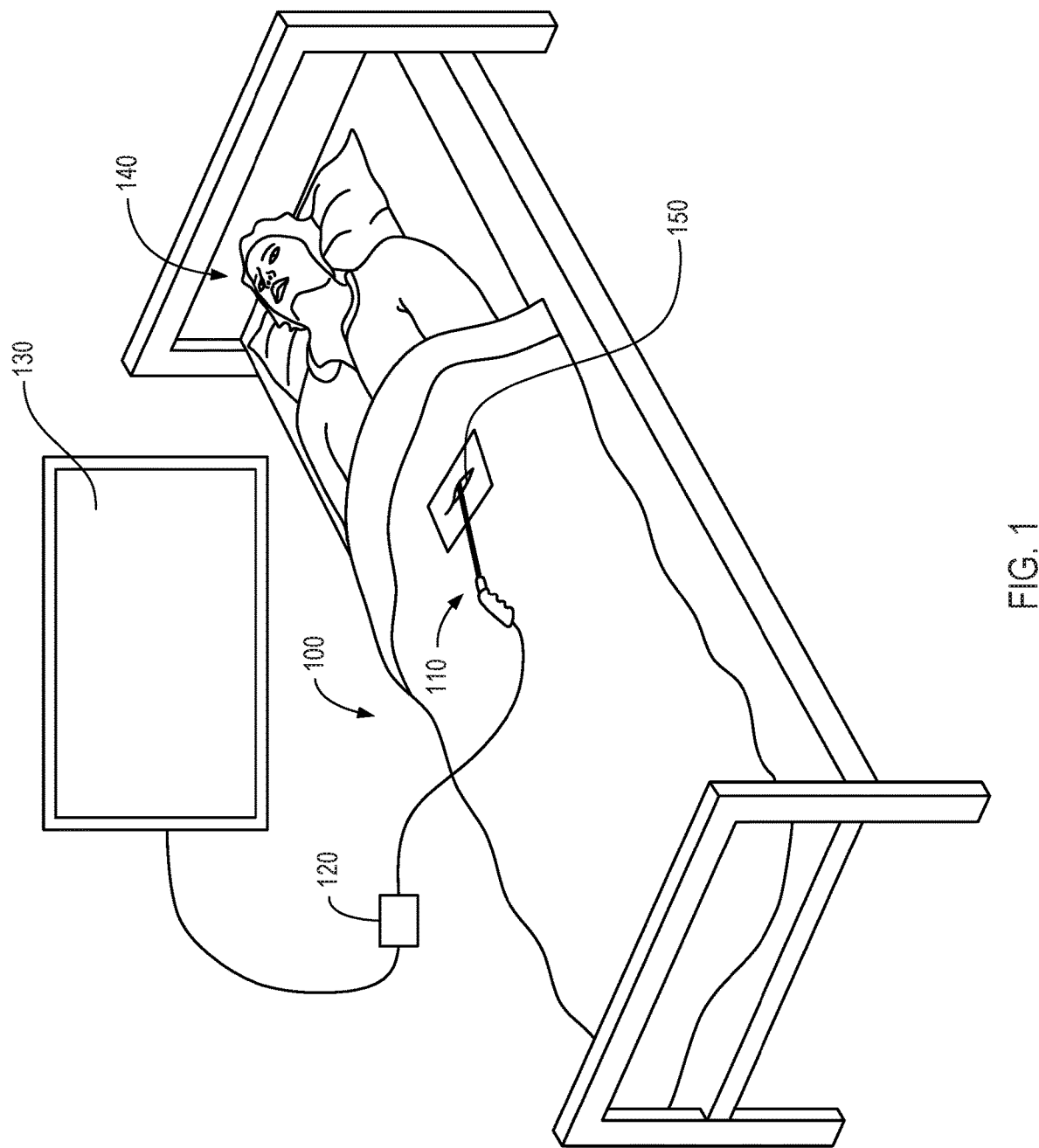
FIG. 1 depicts an illustration of an laparoscopic procedure in accordance with an embodiment of the present invention.

FIG. 1 depicts an illustration of a laparoscopic procedure in accordance with an embodiment of the present invention. In particular, FIG. 1 depicts a laparoscopic procedure being performed on a patient 140 using an implementation of a laparoscopic system 100 in accordance with an embodiment of the present invention. Specifically, a laparoscope 110 is being inserted into port 150 within the patient's 140 abdomen. The laparoscope 110 is in communication with a dongle 120, which dongle 120 is transmitting image data to a television display 130. The transmitted image data can comprise information that is received from the laparoscope 110 that is inserted within the patient's 140 abdomen.

In at least one embodiment, the dongle 120 can comprise one or more common output ports. For example, the dongle 120 may be in communication with the television display 130 through an HDMI port. As such, the television display 130 need not be a specially designed component, but can instead be an off-the-shelf television set. Similarly, the dongle 120 can comprise a common computer input/output port, such as a USB port. As such, the dongle 120 can be in communication with an external computing device through the USB port. Accordingly, the dongle 120 can provide a communications port that communicates to a general-purpose computer or mobile device, such as a tablet or smartphone, and does not require a proprietary processing stack.

Additionally, the dongle 120 can comprise an integrated processing unit. In at least one implementation, the integrated processing unit can comprise a field programmable gate array (FPGA), a microcontroller, a programmable integrated circuit, and/or any other type of processing unit. The processing unit can be configured to receive image data from the laparoscope 110 and perform various processing functions on the image data. For example, the processing unit can format image data to various video and image formats that are readable by the devices that can connect to the dongle 120 through the dongle's various ports.

The processing unit may also be configured to perform various image processing tasks on the received image data. For instance, the processing unit may perform color interpolation operations, color saturation and correction operations, noise filtering, gamma correction, and other similar image processing functions on the received image data.

In one embodiment, the processing unit performs white balancing. The white balance may be pre-calibrated based on the known light spectrum of the LED used in the borescope. The processing unit may also include one or more buttons for user controlled white balance, exposure, gain, zoom, or a macro setting.

In some embodiments, the processing unit may also include a user interface (UI) module for generating display information to be transmitted to the display. For example, one or more of the settings of the borescope may be displayed as an image on the display such that the user can observe and/or change the settings. Generating the UI from the processing unit allows the video image to be displayed on generic TVs or monitors.

As depicted in FIG. 1, some embodiments may comprise a medical borescope system that is highly mobile and highly compatible with commonly available devices. For example, in contrast to requiring a customized medical suite containing a proprietary processing stack, implementation of medical borescope systems as depicted in FIG. 1 can communicate with standard television displays, and only require a small, easily portable dongle for processing. Accordingly, those of ordinary skill in the art will appreciate the benefit that such a system can provide medically impoverished areas and field hospitals where expensive and heavy equipment is not easily accessible.

In some embodiments, the laparoscope may be configured such that it does not connect to an external light source. The light source for laparoscopic system 100 may instead be positioned within the laparoscope 110. In some such embodiments, the light source may be positioned at the distal end of the laparoscope 110 to directly illuminate the subject's tissue. In some embodiments, the illumination may be provided without the use of a light pipe or fiber optics, which reduces the complexity of the lighting system and avoids diffusion of light.

Figure 2:
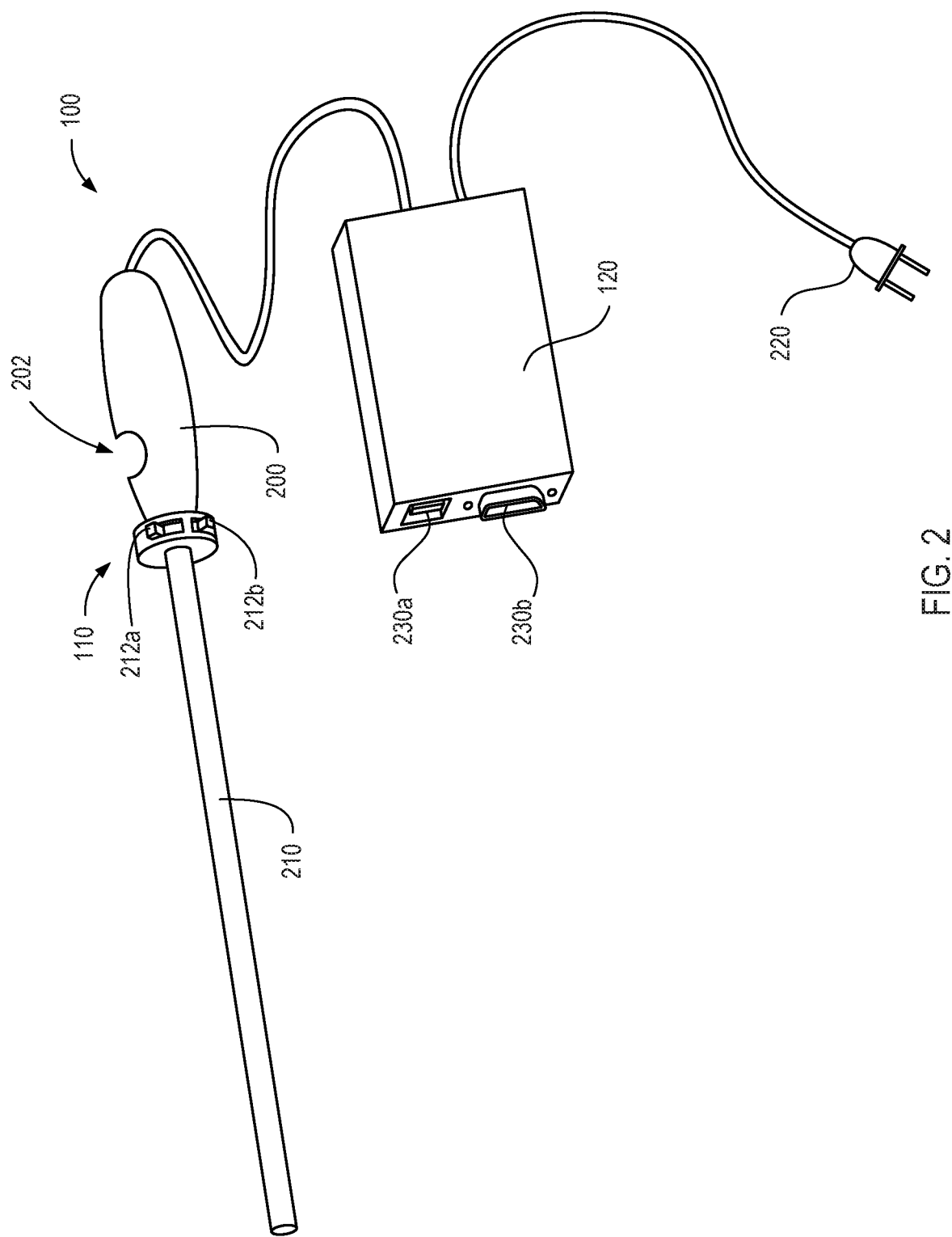
FIG. 2 depicts a laparoscope in accordance with an embodiment of the present invention.

Continuing with the figures, FIG. 2 depicts a laparoscopic system 100 in accordance with an embodiment of the present invention. The depicted laparoscopic system 100 includes a laparoscope 110 and a dongle 120. The depicted laparoscope 110 further includes a borescope tube 210 connected to a handle body 200. The handle body 200 can comprise one or more input components 212a, 212b. The input components 212a, 212b can be used by a medical professional to adjust various attributes of received image data in real time. For example, a medical professional may be able to manipulate white balance, focus, or zoom using a sliding switch or knob 212a, 212b that is positioned on the handle body 200 for easy access. In other embodiments, the laparoscope 110 may have no user actuated features (e.g., no buttons), which reduces the cost and complexity of cleaning and sterilization. In this embodiment, various aspects of the device may be controlled by a processing unit.

In some embodiments, handle 200 may comprise a shape, feature, or element that allows a user, by tactile feel or visual inspection for example, to easily determine which side of the device is up and which side is down. For example, in the embodiment of FIG. 2, a notch 202 is provided so that a user can grab handle 200 and immediately and/or easily feel which side is up, which may be useful in providing images at a desired orientation. Other embodiments are contemplated in which notch 202 may be replaced with another feature or element, such as a protrusion or the like. Alternatively, handle 200 may comprise a non-symmetrical shape, such as is shown in the embodiment of FIGS. 11A and 11B, which is discussed in greater detail below. Such a shape may allow a user to hold the handle and be able to determine based upon tactile feel alone, whether the device is being held in a preferred rotational orientation. In still other embodiments, a visible element, such as an image, marking, or the like, may be provided on just one side of the handle 200 to allow for immediate visual confirmation of the rotational orientation of the device. Notch 202, along with the other elements, features, or components mentioned herein that allow a surgeon or other user to determine, by visual inspection and/or tactile feel, a rotational orientation of the handle, are all examples of means for confirming a rotational orientation of a borescope handle.

In the depicted embodiment, the laparoscope 110 is in communication with a dongle 120 through a wired connection. As shown, the dongle 120 can be positioned communicatively intermediate the laparoscope 110 and a display device. In various embodiments, the dongle 120 can comprise a variety of different size and form factors. For example, the dongle 120 can comprise any dimensions that result in a volume equal to or less than 16 cubic inches. In contrast, on the lower end, the dongle 120 can comprise any dimensions that result in a volume of equal to or greater than 1 cubic inch. Further, the dongle 120 can comprise a volume between 2 cubic inches and 14 cubic inches, 4 cubic inches and 12 cubic inches, 6 cubic inches and 10 cubic inches, or 8 cubic inches and 9 cubic inches.

As disclosed above, the dongle 120 can comprise a processing unit that is configured to perform various image processing tasks. For example, the image processing unit may format received image data into formats that are readable at various output ports 230a, 230b. The dongle 120 can also comprise a multicasting module that enables the delivery of data simultaneously to multiple output devices. For example, the dongle 120 may be able to output image data to a plurality of high definition television displays that are positioned at different locations around a medical room. Additionally, the multicast module may be configured to broadcast simultaneously over a plurality of different output port types disposed on the dongle 120. For example, the multicast module may transmit the image data simultaneously over both an HDMI output port and a VGA out port. As such, a plurality of different display types can be connected to the dongle 120 and receive from the dongle 120 the same information over each respective output port type. In some embodiments, image data may be simultaneously unicast or multicast over a network, such as an Ethernet, WIFI, or fiber optic network, for example.

The dongle 120 may be connected to the laparoscope 110 and/or the display 130 (FIG. 1) using cords of a particular length to minimize cord tangling but place the dongle in a desired location relative to the patient. For example, in some embodiments, the cords are selected to place the dongle outside the sterile field. In some embodiments the data cable between the laparoscope and the dongle may be greater than 2, 4, or 6 feet and/or less than 14, 12, or 10 feet, or within a range of the foregoing. In some embodiments, the dongle may be connected to a monitor with a cord that is less than 14, 10, 8, 4, 2, or even 1 foot. The dongle may be encased in a protective casing (e.g., rubber casing) that protects the dongle sufficiently to place it on the floor where it may be stepped on. Alternatively the dongle may include a clip for attaching the dongle to a bedpost. Additional alternative means for coupling the dongle to an exterior device or element may comprise screws and/or mounting plates for coupling the dongle to a monitor or mounting the dongle on a standard rack.

Figure 4A:
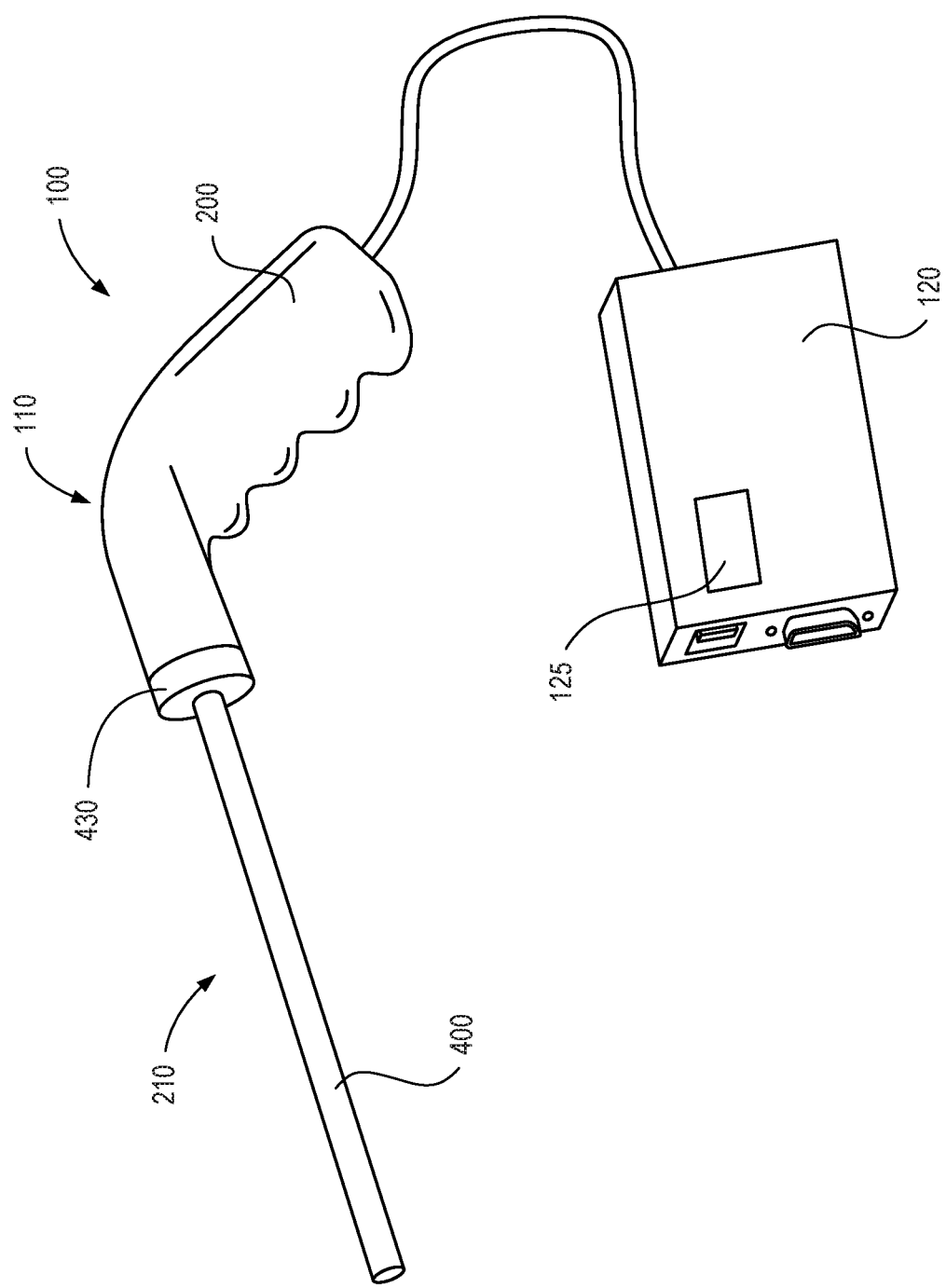
FIG. 4A depicts a medical borescope device with a removable borescope tube in accordance with another embodiment of the present invention.

Additionally, in at least one implementation, the dongle 120 can comprise an electrical outlet 220 that is configured to provide power to the dongle 120, the laparoscope 110, and/or a display. In alternate embodiments, the dongle 120 can comprise an integrated power source, such as a battery 125, as illustrated in FIG. 4A, that may be used to power the dongle 120 and/or the laparoscope 110. In some embodiments, battery 125 may be rechargeable. Further still, in at least one implementation, the dongle 120 can comprise a port that can communicate with and receive power from an external device, for example, a USB port in communication with a computer.

Figure 3:
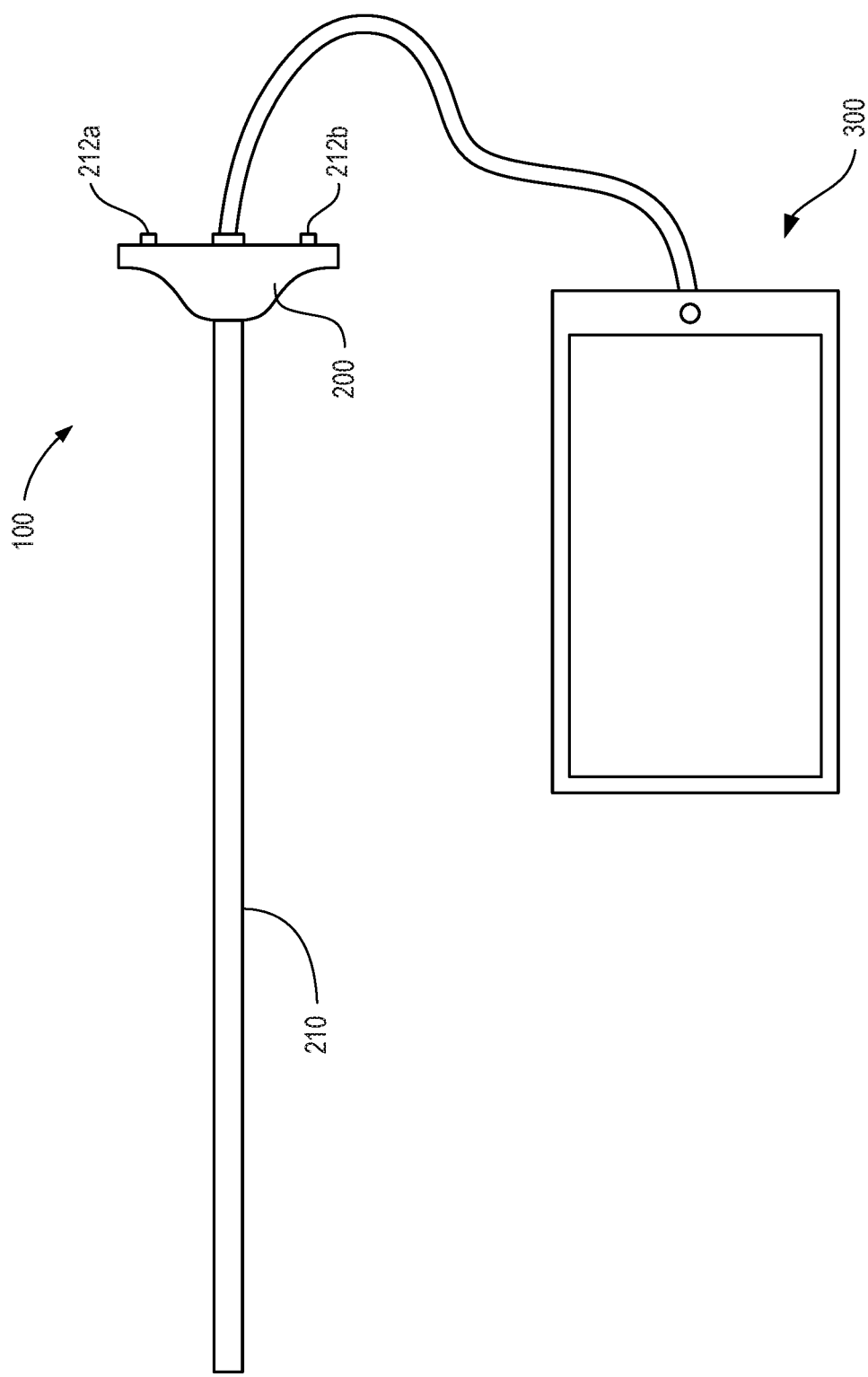
FIG. 3 depicts an alternate embodiment of a laparoscope.

FIG. 3 depicts an alternative embodiment of a laparoscopic system. In this implementation, the laparoscopic system 100 comprises an alternative shape for a handle body 200, alternate configurations for the input components 212a, 212b, and a mobile computing device 300, instead of a dongle. In alternate embodiments, instead of a mobile computing device 300, the laparoscopic system 100 may be in communication with a desktop computer.

In at least one embodiment, the mobile computing device 300 may comprise a tablet computer, a smart phone, or a laptop computer. The mobile computing device 300 can be configured to perform various image processing tasks on the image data received from the laparoscopic system 100. For example, the mobile computing device 300 can provide various viewing features, image editing features, video and image storage features, data sharing features, and other similar computer enabled functions. Additionally, when a medical professional makes adjustments to the input components 212a, 212b the adjustments may be received by the mobile computing device 300, which can initiate any necessary adjustments that need to be made within the laparoscopic system 100 to execute the adjustments received from the medical professional.

In order to communicate with the laparoscopic system 100, the mobile computing device 300 may comprise a custom software application. The software application may be configured to communicate with the laparoscopic system 100 and to provide various laparoscopic specific functions. Additionally, the software application may comprise a streaming functionality that allows the images received by the mobile computing device 300 to be streamed to a remote location. In this way, a medical professional can participate virtually in the laparoscopic procedure, even if that medical professional is at a remote location.

Turning now to FIGS. 4A-4C, FIG. 4A depicts an implementation of a laparoscope with a removable borescope tube in accordance with an embodiment of the present invention. The system 100 depicted in FIG. 4A comprises a borescope tube 210, a handle body 200, and a dongle 120, as recited above. Additionally, in some embodiments, the laparoscopic system 100 may comprise an interchangeable borescope 210. For example, the borescope 210 of FIG. 4A includes an interchangeable tube portion 400 and an attachment point 430. In particular, the interchangeable tube portion 400 of FIG. 4A comprises a laparoscope tube 400 of a specific diameter and length.

FIGS. 4B and 4C depict various embodiments of interchangeable tube portions 410, 420. Interchangeable tube portion 410 comprises a laparoscopic tube portion 410 that is of a longer and narrower dimension than laparoscopic tube portion 400 depicted in FIG. 4A. In contrast to the laparoscopic tubes 400, 410 depicted in FIGS. 4A and 4B, FIG. 4C depicts an endoscope tube portion 420. Both the laparoscopic tube portion 410 in FIG. 4B and the endoscopic tube portion 420 in FIG. 4C can communicate with the same attachment point 430.

In some embodiments, one or more tube portions may comprise a non-conductive material, such as a plastic or ceramic material, that may serve as a shield from other devices, such as cauterization devices or other electrosurgical devices. Such material may make up the entire tube portion, or a portion of the tube. In some embodiments, a shielding tube may be positioned concentrically over another tube. In some embodiments, other shielding techniques/features, such as a Faraday cage, may be incorporated within or otherwise adjacent to the non-conductive tube or tube portion.

Accordingly, in some implementations, a medical professional can choose between a variety of different tube portions to meet the needs of a particular procedure. For example, an embodiment of a borescope system as depicted in FIG. 4A can perform laparoscopic procedures that require a variety of different borescope lengths, diameters, stiffnesses, material types (e.g., steel, plastic, etc.), and/or surgical tools integrated into the laparoscope. In at least one implementation, the laparoscope tube portions can also be available in a variety of different levels of deformability, such that particular laparoscopic tube portions are rigid, while others comprise significant flexibility.

Similarly, some implementations can perform a variety of different endoscopic procedures that likewise require different borescope attributes. For example, in some embodiments and implementations, a single medical borescope system may be used with endoscopes that are sized for infants, children, and/or adults. Additionally, various different features and abilities can be incorporated into the individual endoscopes such that a medical practitioner can select a particular endoscope tube based upon the optics in the tool, specific surgical tools incorporated into the tool, specific sensors incorporated into the tool, dimensions of the tool, material of construction, and/or other similar features and abilities.

Additionally, implementations of a borescope system as disclosed in FIGS. 4A, 4B, and 4C provide a system where the individual borescope portions 400, 410, 420 can also be easily sterilized and clean. For example, in at least one implementation, the borescope portions 400, 410, 420, are disposable after each procedure, such that new, sterilized borescope portions 400, 410, 420 are used for each procedure. In an alternate embodiment, the borescope tube portions 400, 410, 420 are removable such that they can easily be cleaned and sterilized.

While FIG. 4A depicts an attachment point 430 that extends from the handle body 200, in at least one implementation, the borescope tube portions 400, 410, 420 interchangeably connect directly to the handle body 200. In either case, the attachment point 430 may be located such that no portion of the attachment point will come in contact with non-sterile surfaces. In this way, the contact point 430 and the handle body 200 may not require the same level of sterilization as the borescope tube portions 400, 410, 420.

Further, in a least one implementation, the borescope tube portions 400, 410, 420 are integrated into a single structure such that the borescope tube portions 400, 410, 420 may not removable from the handle body 200. In this case, the handle body 200 can be interchangeably connected to a dongle 120. As such, various types of laparoscopes and endoscopes, including their respective handle bodies 200, can be interchangeably connected to a single dongle 120.

Figure 5:
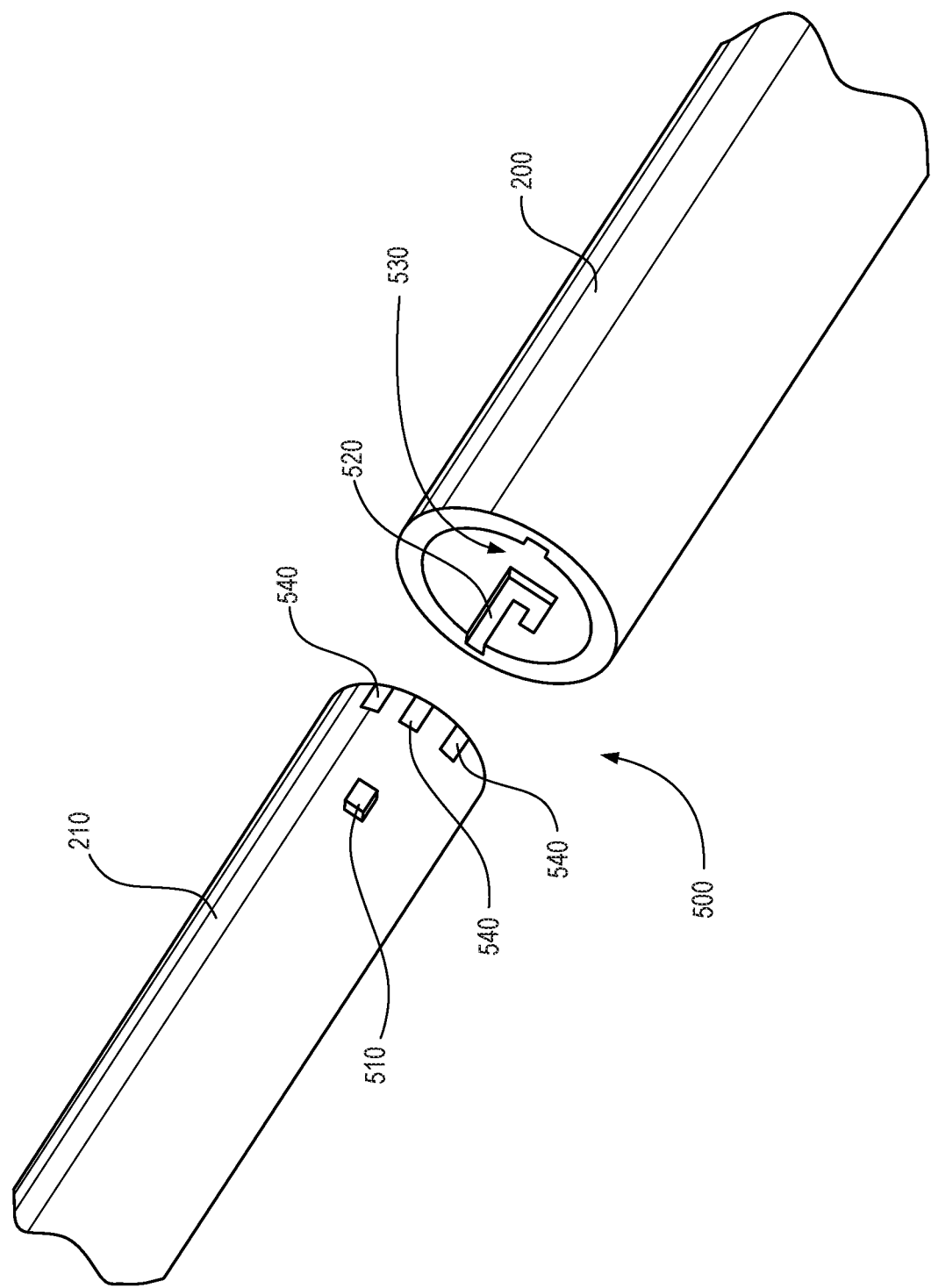
FIG. 5 depicts an embodiment of an interchangeable borescope tube being connected to a handle body.

FIG. 5 depicts an implementation of an interchangeable borescope tube being connected to a handle body in accordance with another embodiment. In particular, FIG. 5 depicts a borescope tube 210 and a handle body 200 being connected through a pin and latch connection 500. The pin and latch connection 500 may comprise one or more pins 510 that extend from the body of the borescope tube 210. The one or more pins 510 may be receivable by one or more latches 520 that are formed within a receiving hole 530 in the handle body 200. The one or more pins 510 and the one or more latches 520 may be spaced apart such that each of the one or more pins 510 is only receivable by specific latches 520, thus requiring the borescope tube 210 to have a particular orientation with respect to the handle body 200.

Various alternate embodiments may comprise connectors other than a pin and latch connection 500. For example, the borescope tube 210 and the handle body 200 can be connected through a threaded connection, a clamp connection, a press fit connection, or any other common connection type. In at least one implementation, it may be desirable for the connection type to limit rotational movement between the borescope tube 210 and the handle body 200. This may be necessary to prevent the borescope tube 210 from disconnecting from the handle body 200 when in use.

In at least one implementation, the borescope tube 210 can also comprise electrical connection points 540 disposed around a bottom portion of the borescope tube 210. The electrical connection points 540 can be configured to receive power from the handle body 200 and to provide a communication path between the instruments within the borescope tube 210 and components within the handle body 200. While the electrical connection points 540 are depicted as electrically conductive contact pads disposed around a bottom circumference of the borescope tube 210, in other implementations, the electrical connection points 540 can be positioned anywhere where the borescope tube 210 contacts the handle body 200. Additionally, the electrical connection points 540 can comprise pin and socket connections, magnetic connections, inductive connections, and any other common connection type. Similarly, if fiber optics or some other communication medium is used, proper connection points can also be incorporated into the borescope tube 210 and handle body 200.

Figure 6A:
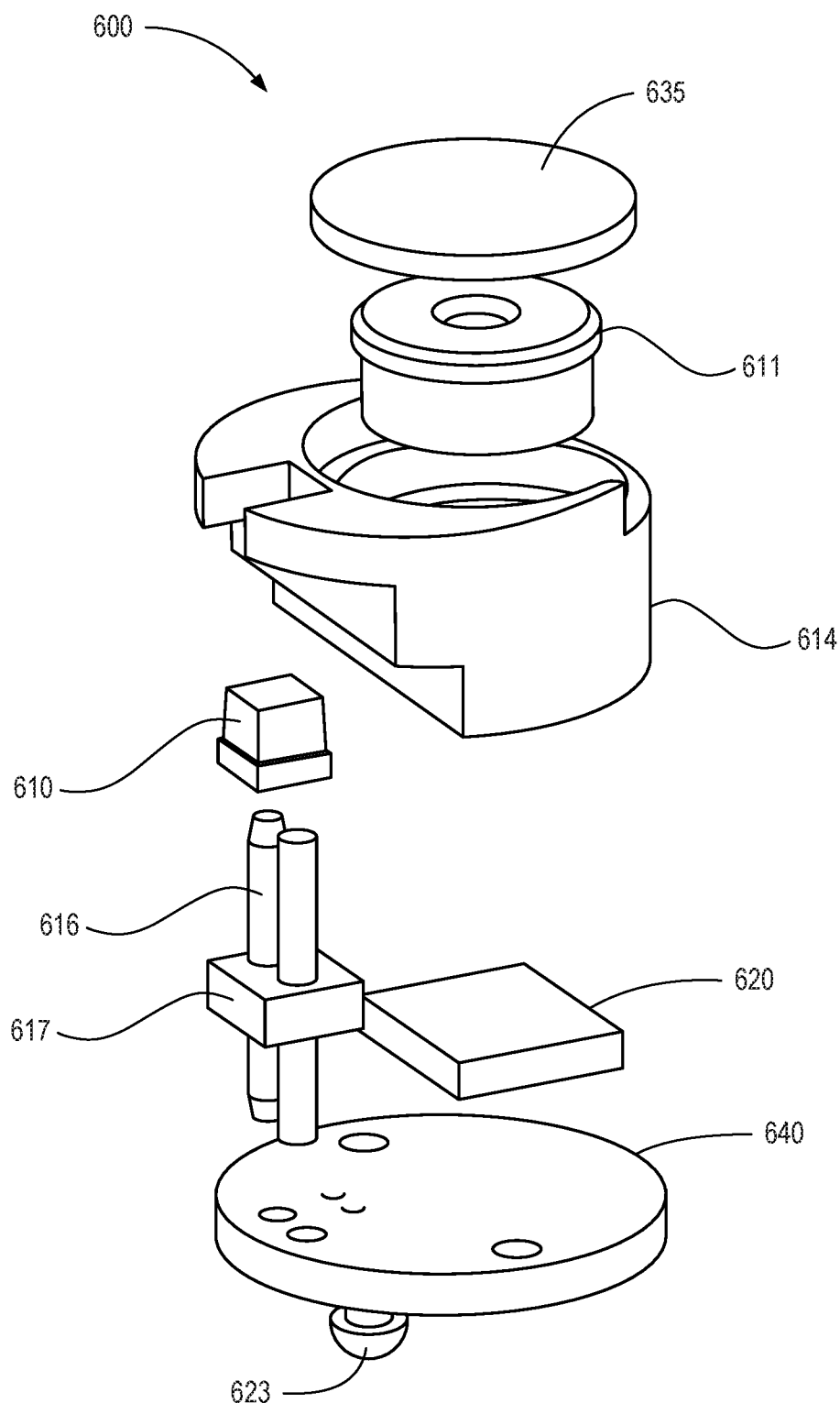
FIG. 6A depicts an exploded view of an assembly configured to be positioned in a tip of a borescope tube and/or to form the tip of a borescope tube in accordance with an embodiment of the present invention.
Figure 6B:
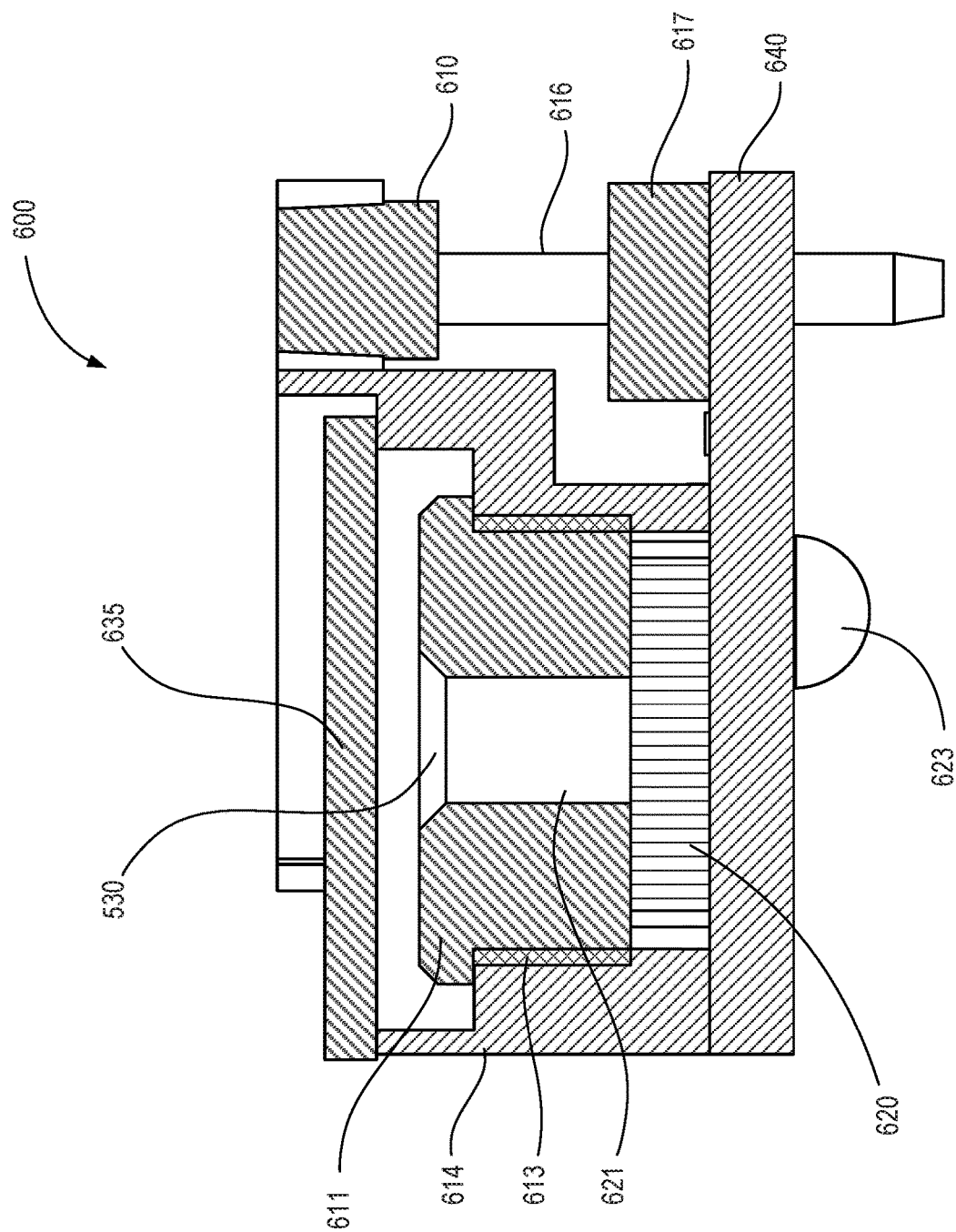
FIG. 6B depicts a cross-section of the tip of the borescope tube depicted in FIG. 6A.
Figure 7:
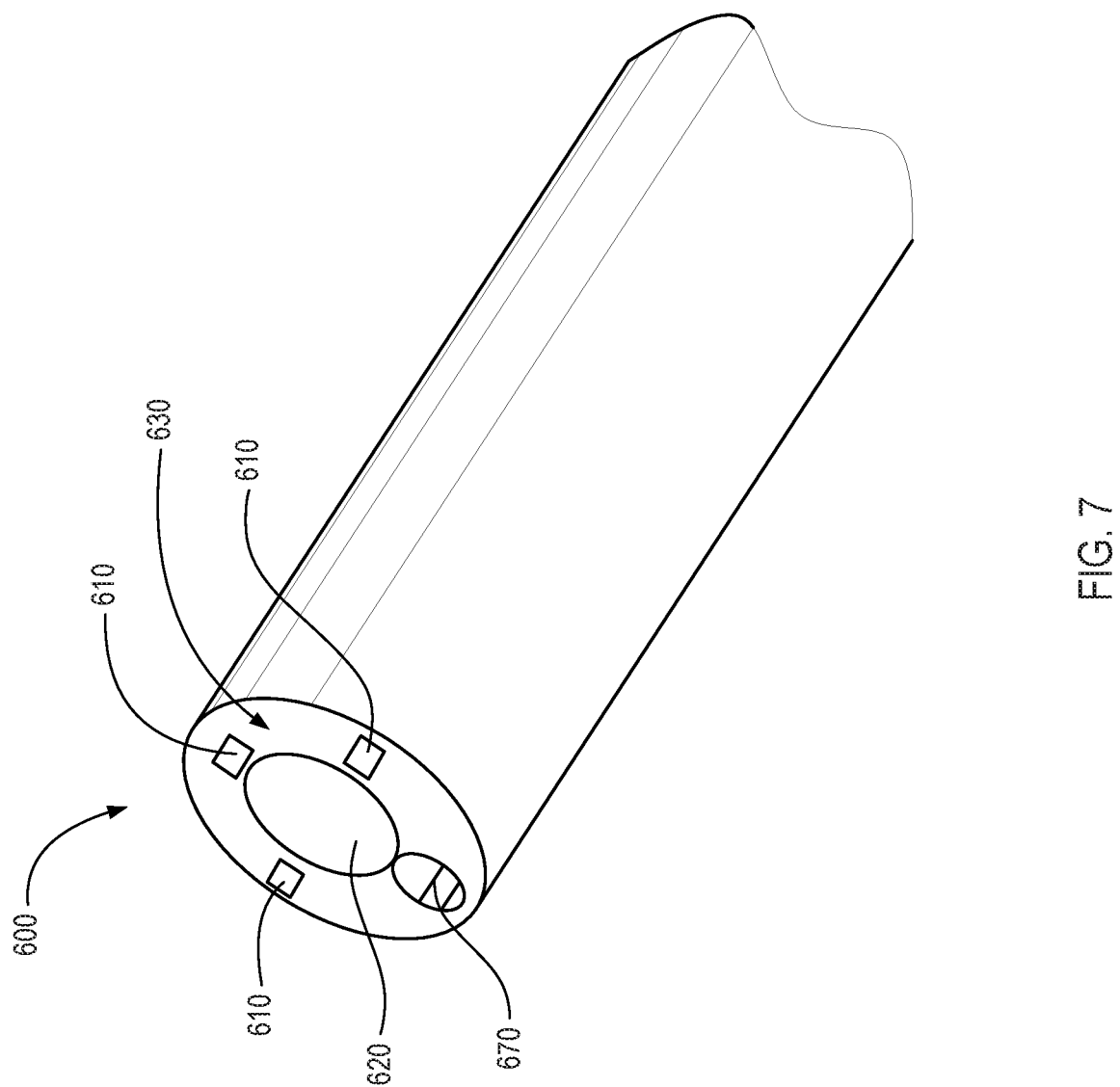
FIG. 7 depicts another embodiment of a tip of the borescope tube in accordance with an embodiment of the present invention.

FIGS. 6A-6B and FIG. 7 depict an embodiment of a tip 600 of a borescope tube in accordance with another embodiment. The depicted tip 600 comprises the portion of the borescope tube that is distal from the handle body 200, and is the portion of the borescope that is foremost inserted into a patient. The tip 600 can comprise various features including one or more LED lights 610, image sensors 620, through ports 670, and other medical borescope components. In at least one embodiment, the one or more LEDs 610 can comprise a variety of different colors and intensities. The different LEDs 610 may be individually addressable and controllable by a medical professional or may be automatically controlled by a processing unit within the borescope tube, within the handle body 200, or within the dongle 120.

FIGS. 6A and 6B illustrate example componentry that can be used in a tip 600 of a borescope according to some embodiments of the invention. FIG. 6A illustrates an exploded view and FIG. 6B illustrates a cutaway view. A tip 600 includes a housing 614, lens assembly 611, cover glass 635, light emitting diode (LED) 610, wiring 616, spacing mount 617, image sensor 620, printed circuit board (PCB) 640 and assembly screw 623. Sensor 620 may be mounted directly to PCB 640 and PCB 640 may be mounted to housing 614 to secure PCB 640. Lens assembly 611 includes an optical component 530 (i.e., a lens) that is mounted a particular distance from image sensor 620 to provide proper focus. Threads 613 allow lens assembly 611 to be moved relative to housing 614 to change the spacing 621 between image sensor 620 and optical element 530. Cover glass 635 may be sealed to housing 614 to prevent fluids in a patient from contacting lens assembly 611. Cover glass 635 may also protect lens assembly from being bumped, which (if not protected) could move the lens out of focus.

The image sensor 620 can comprise a custom-made CMOS sensor, an off-the-shelf CMOS sensor, or any other digital image capture device. Additionally, the image sensor 620 can be configured to capture and video in a variety of different resolutions, including, but not limited to 720p, 720i, 1080p, 1080i, and other similar high resolution formats. The image sensor 620 may also comprise a pixel size greater than 0.8 µm, 1 µm, or 2 µm and/or less than 4 µm, 3 µm, 2 µm, or within a range of any of the foregoing upper and lower sizes.

LED 610 may be mounted to housing 614. In a preferred embodiment, LED 610 is mounted essentially flush with the end of housing 614 so as to minimize tunneling of the light. LED 610 may be mounted off of PCB 640 to facilitate placing LED 610 flush with housing 614. For example, LED 610 may be within 3 mm, 2 mm, or 1 mm of the end of housing 614. Mounting LED 610 off of PCB 640 can be achieved using a wire 616 to power LED 610. LED 610 may be mounted to housing 614 using an optically pure epoxy or other suitable methods. A cover glass may also be used over LED 610 (not shown).

In some embodiments, LED 610 may be mounted to PCB 640 and a light guide may be used to channel light to an opening in distal end of tip 600. In one embodiment, the light guide may be less than 20 cm, 10 cm, 5 cm or 2 cm. The LED 610 is preferably placed in tip 600, but with the use of a light pipe may also be placed at an intermediate location within the borescope tube or within the handle of the borescope. However, the LED 610 is placed within the borescope such that no external cables to a light source need to be attached. Placing the LED 610 within the borescope minimizes the distance the light has to travel and eliminates the possibility of a light source with a different emission spectrum from being attached. The LED 610 embedded in the borescope can then be white balanced at the time of manufacturing to ensure proper tissue color with minimal or no input from the user.

The portion of housing 614 that surrounds LED 610 is used to optically isolate LED 610 from lateral exposure of light to image sensor 620. For example, LED 610 is isolated laterally from cover glass 635. This isolation prevents light from diffusing or reflecting back into cover glass 635 or image sensor 620 prior to being reflected off tissue. Because of the close proximity of the LED 610 and image sensor 620 this isolation is important to achieve a usable signal to noise ratio. LED 610 is preferably mounted distal to image sensor 620 and even more preferably distal to cover glass 635.

In at least one implementation, the LEDs 610 and image sensor 620 can be attached to a common printed circuit board 640. The LEDs 610 and image sensor 620 can communicate to the handle body 200 through one or more wires. Additionally, the LEDs 610 and image sensor 620 can receive power through the plurality of wires. In a preferred embodiment image sensor 620 and/or PCB 640 can preprocess pixel data and output a serialized data stream that can be transmitted over a relatively large distance (e.g., greater than 50, 75, or 100 cm). In a preferred embodiment the image data output from tip 600 is serialized data from a MIPI or LVDS interface. The image data may be at least 8 or at least 12 bit, and the data may be RGB data or Bayer data.

Various embodiments of the present invention can provide a variety of optic configurations. For example, in at least one embodiment, the optics can be configured as a fixed zero-degree lens 630 with a small aperture, such that the optics comprise a high depth of field. Additionally, the optics can be configured such that it focuses at 10 cm instead of at 1 m, which is typical of many conventional CMOS optical systems. In particular, the optics may comprise approximately a 90-degree field of view with approximately a 15 mm near depth of field, and approximately a 100 mm far depth of field.

Additionally, in at least one embodiment, the optics may comprise a fish-eye lens or a wide-angle lens. In such an embodiment, the dongle 120 may also comprise image processing components configured to smooth out the images received from a wide-angle lens or a fish-eye lens such that at least a portion of the distortion from the lens is removed from the final image. In at least one embodiment, interchangeable borescope tubes are available with a variety of different optics, such that a medical practitioner can select a particular borescope tube based upon desired optical properties.

In at least one implementation, the borescope has a fixed lens with a depth of field that spans a range of at least 30 cm, 50 cm, or 70 cm, and/or less than 120 cm, 100 cm, or 90 cm and/or within a range of the foregoing. The bottom of the focal range may be less than 20 cm, 15 cm 10 cm, or 5 cm and the upper boundary of the focal range may be greater than 50 cm, 70 mm, 90 cm, or 110 cm. For purposes of this disclosure, the lens may be considered in focus where the lens produces a spot size of less than 2 pixels.

The F # of the lens is selected to provide sufficient light at the selected depth of field. The lens may have an F # greater than or equal to 2.5, 3.5, 5.5, 7.5, or 10.

FIGS. 6 and 7 show a scope with a zero degree angle. However, the lens may also have an angled lens (i.e., relative to the axis of the borescope tube). The lens angle may be greater than or equal to 15, 25, or 45 degrees and/or less than or equal to 65, 50, or 35 degrees. The angle for the field of view may be greater than 60, 75, or 90 degrees and/or less than 110, 100, or 90, or within a range of the foregoing. In one embodiment, the optics system can comprise a focal length of approximately 2 mm and an F # of approximately 2.4.

In some embodiments, software image rotation may be used to preserve a preferred orientation of the image on the display while the user rotates the scope. In some such embodiments, the system and/or device may be configured such that image rotation may be controlled on the device, such as by way of a dial on the handle. In some embodiments, one or more rotation, orientation, and/or tilt sensors, such as accelerometers, may be provided to facilitate desired image orientation/rotation.

FIG. 7 illustrates an embodiment having three LEDs circumferential to image sensor 620. A through port 670 may comprise a passageway that extends at least partially up the length of the medical borescope tube. In at least one embodiment, the through port 670 can be configured to allow a medical professional to insert a medical tool through the through port 670 and into a patient. For example, a medical professional may insert a biopsy tool through the through port 670 such that a particular tissue, identified by the borescope, can be removed for biopsy.

Figure 8:
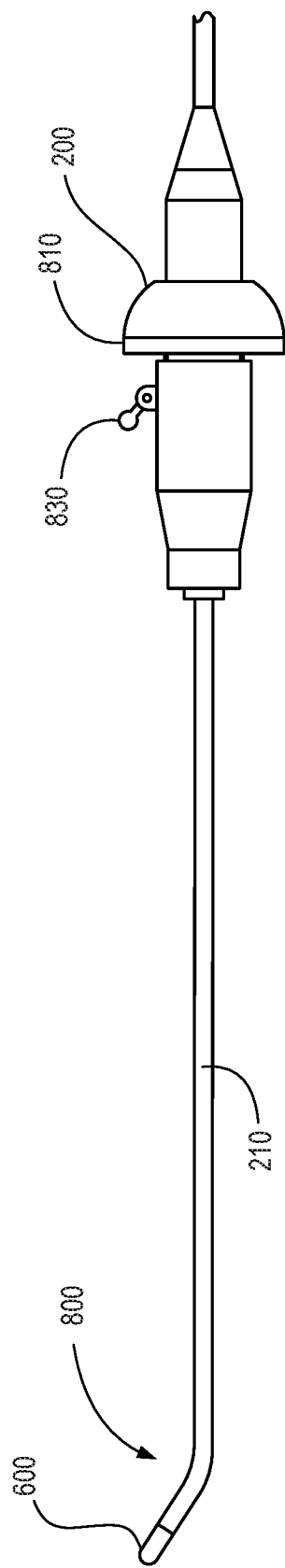
FIG. 8 depicts an embodiment of a laparoscope with an articulable tip.

In addition to providing various optics that influence a medical practitioner's view within a patient, in some embodiments, a medical borescope may comprise an articulable portion. For example, FIG. 8 depicts another embodiment of a laparoscope having an articulable tip. Specifically, the borescope tube 210 comprises an articulation point 800 that allows the tip 600 to be pointed in a direction other than parallel to the borescope tube 210. In at least one implementation, the articulation point 800 can articulate up to 90 degrees in any direction with respect to the borescope tube 210. As such, the tip 600 can be mobile within a complete hemisphere extending radially outward from the articulation point 800.

While various different schemes for controlling the articulation of the tip 600 can be used, as an exemplary scheme, one or more sliders 810 can be positioned along the handle body 200. In at least one embodiment, the slider(s) 810 can be positioned near one or more input components 212a, 212b that can manipulate various attributes of images received through the medical borescope. Each of the sliders 810 can be configured to articulate the articulation point 800 along a single respective axis. As such, a medical professional, in some embodiments using a combination of sliders 810, can position the tip 600 to be aligned with any point along a hemisphere that extends outward from the articulation point 800.

By controlling the articulation of the tip 600 of the borescope within a patient, a medical practitioner can more easily view various surfaces within the patient. This may provide particular benefit in a fixed lens system—where otherwise the field of view may be limited to directly forward from the tip 600.

Figure 9:
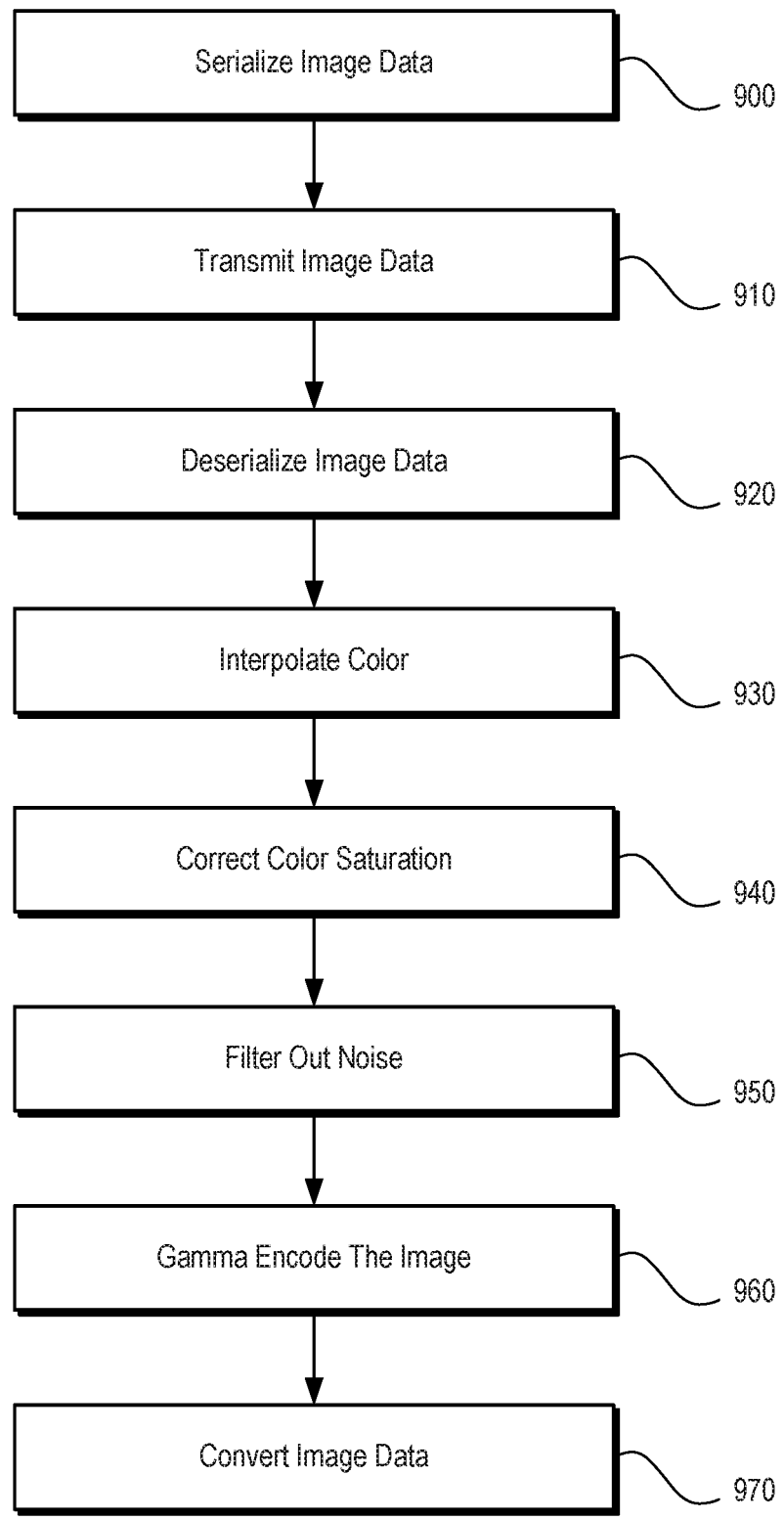
FIG. 9 depicts a sequence of steps in a method for performing an implementation of the present invention.

Accordingly, FIGS. 1 through 8 and the corresponding text illustrate or otherwise describe one or more methods, systems, and/or apparatus for utilizing a medical borescope that comprises interchangeable borescope tubes and digital image sensors within a tip of the borescope tube. Those of ordinary skill in the art will appreciate that the implementations of the present invention can also be described in terms of methods comprising one or more acts or steps for accomplishing a particular result. For example, FIG. 9 illustrates flowcharts of a sequence of acts in a method for processing image data received from a medical borescope instrument. The acts/steps of FIG. 9 are described below with reference to the components and modules illustrated in FIGS. 1 through 8.

For example, FIG. 9 illustrates a flow chart for implementation of a method for processing image data received from a medical borescope instrument, which method can comprise an act 900 of serializing image data. Act 900 includes serializing image data received from an image sensor, wherein the image sensor is disposed in a first end of a medical borescope tube. For example, FIG. 6A depicts a tip 600 of a medical borescope tube 210 that comprises an image sensor 620. Information received through the image sensor 620 is serialized before being transmitted down the medical borescope tube 210.

FIG. 9 also shows that the method can comprise an act 910 of transmitting image data. Act 910 includes transmitting the serialized image data down the medical borescope tube to a second end of the medical borescope tube. For example, FIG. 6A depicts electrical communication pathways connecting the image sensor to a second end of the medical borescope tube 210.

Additionally, FIG. 9 shows that the method can comprise an act 920 of deserializing image data. Act 920 can include deserializing the image data at an image processor, wherein the image processor is located within a dongle that is in communication with the image sensor. For example, FIG. 2 depicts a dongle 120 in communication with a laparoscope 110. The dongle 120 comprises an image processor that receives data transmitted from an image sensor 620 and deserializes the received data.

FIG. 9 also shows that the method can comprise act 930 of interpolating color. Act 930 includes interpolating color from the image data using the image processor. For example, FIG. 2 depicts a dongle 120 in communication with the laparoscope 110. The dongle 120 comprises an image processor that is configured to interpolate color information from the image data that is received from the image sensor 620.

In addition, FIG. 9 shows that the method can comprise act 940 of correcting color saturation. Act 940 includes correcting color saturation using the image processor. For example, FIG. 2 depicts a dongle in communication with the laparoscope 110. The dongle 120 comprises an image processor that is configured to correct color saturation within the image data that is received from the image sensor 620.

FIG. 9 also shows that the method can comprise act 950 of filtering out noise. Act 950 can include filtering noise out of the image data using the image processor. For example, FIG. 2 depicts a dongle in communication with the laparoscope 110. The dongle 120 comprises an image processor that is configured to filter noise out of the image data that is received from the image sensor 620.

Further, FIG. 9 shows that the method can comprise act 960 of gamma encoding the image. Act 960 can include gamma encoding the image data using the image processor. For example, FIG. 2 depicts a dongle in communication with the laparoscope 110. The dongle may comprise an image processor that is configured to gamma encode the image data that is received from the image sensor 620.

Further still, FIG. 9 shows that the method can include act 970 of converting image data. Act 970 can include converting the image data from RGB to YUV. For example, FIG. 2 depicts a dongle in communication with the laparoscope 110. The dongle may comprise an image processor that is configured to convert RGB data received from the image sensor 620 into YUV data.

In addition, to the implementation depicted in FIG. 9, in at least one implementation, instead of processing the data using an image processor disposed within the dongle 120, the data can be sent from the image sensor to a mobile computing device, such as a tablet. In this embodiment, the tablet can be used to perform the necessary image processing and image display.

Figure 10A:
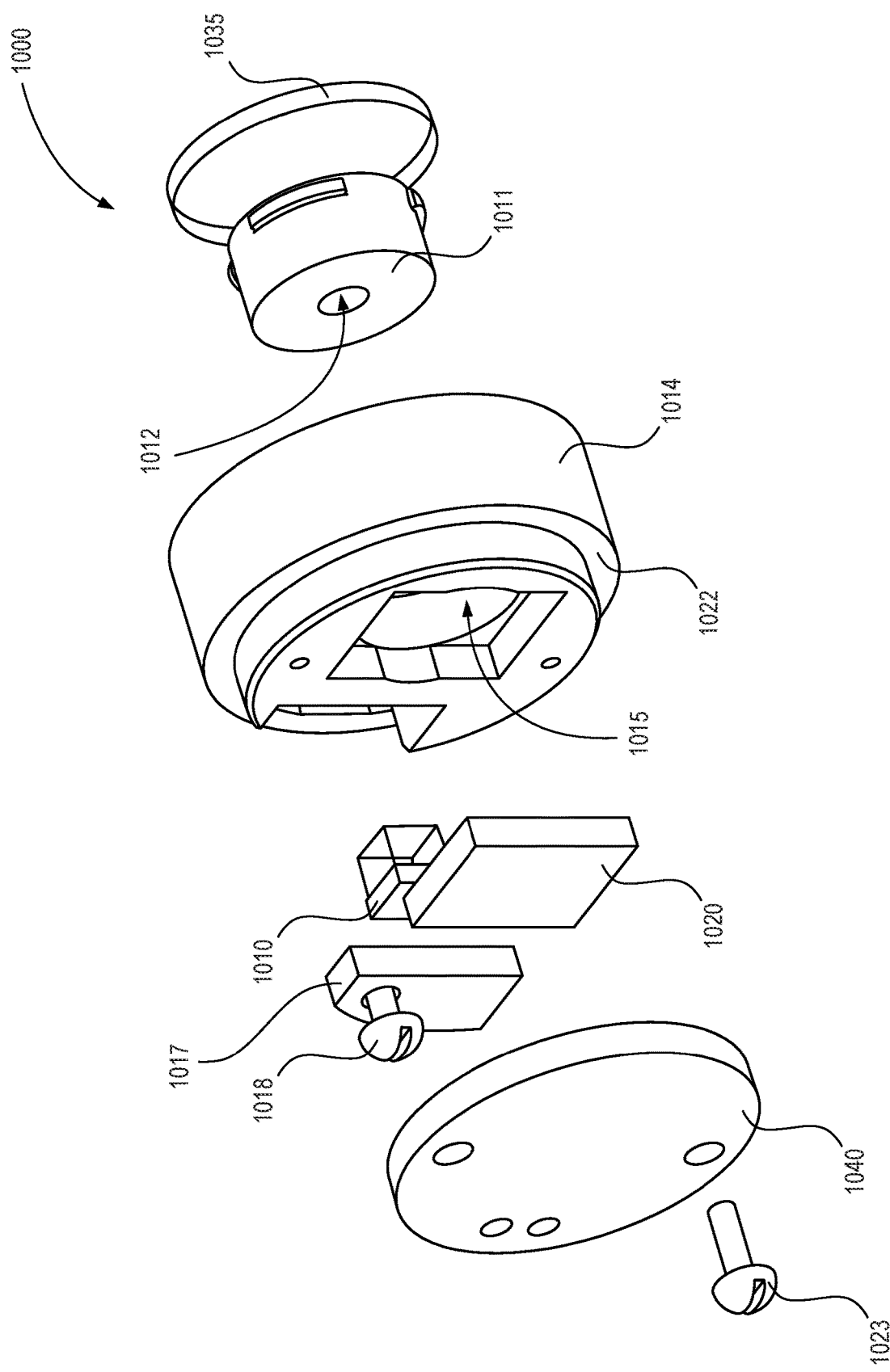
FIG. 10A is an exploded view of another embodiment of a tip assembly configured to be positioned within and/or to form the tip of a borescope tube.
Figure 10B:
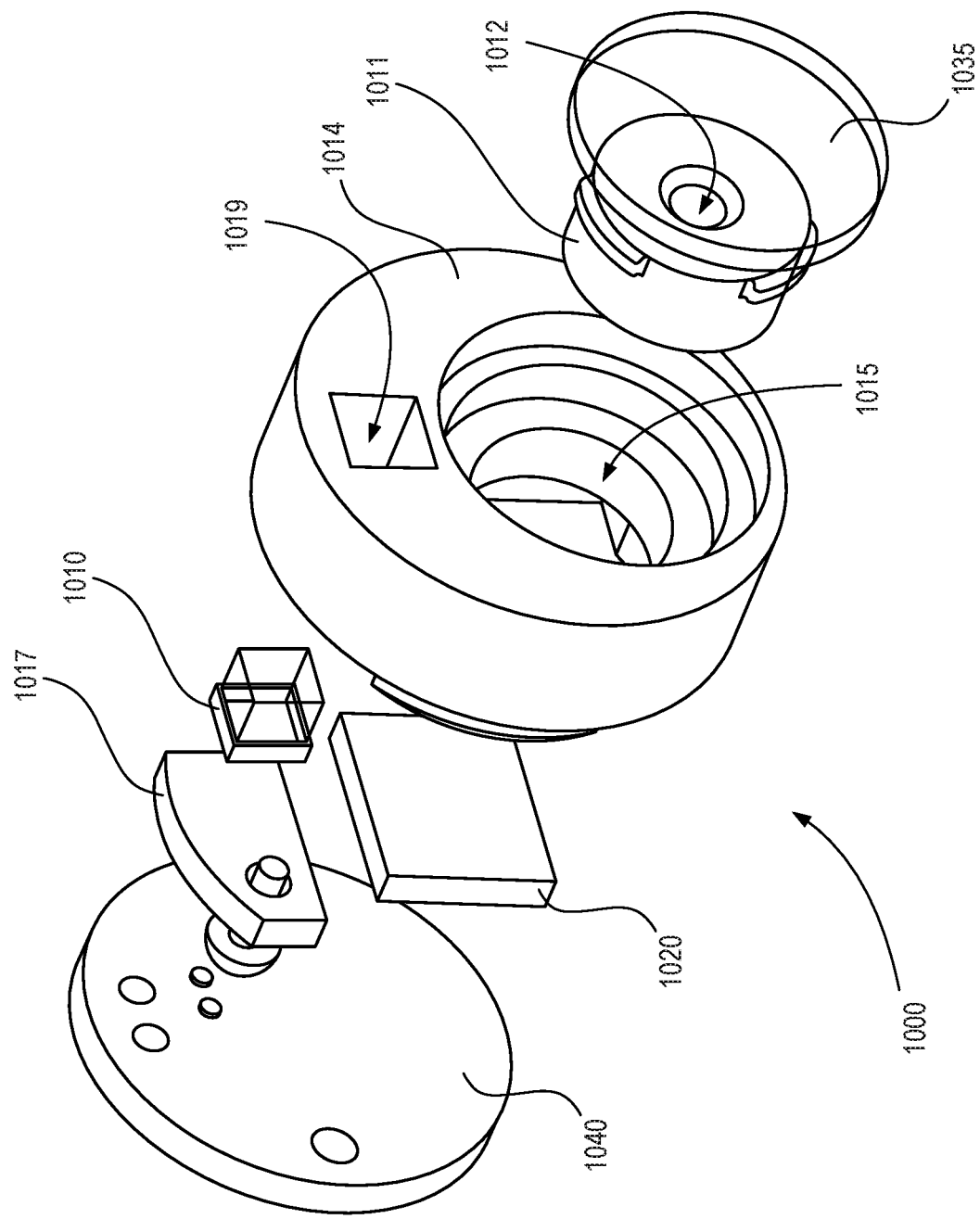
FIG. 10B is another exploded view of the tip assembly of FIG. 10A.

FIGS. 10A and 10B are exploded views of another embodiment of a tip assembly 1000 configured to be positioned within and/or to form the tip of a borescope tube. In the depicted embodiment, tip assembly 1000 is configured to be inserted into the distal end of a tube by inserting internal collar 1022 of housing 1014. Of course, a variety of alternative embodiments are contemplated, such as inserting assembly 1000 around the exterior of a borescope tube or otherwise coupling assembly 1000 with a distal end of a borescope tube.

As with tip assembly 600, tip assembly 1000 may be coupled with a handle body, such as handle body 200, and would typically comprise the portion of the borescope that is initially inserted into a patient. Tip assembly 1000 comprises one or more light sources 1010, such as LED lights, one or more image sensors 1020, and/or other medical borescope components. Light sources 1010 may be manually controllable by a medical professional or may be automatically controlled by a processing unit within the borescope tube, the handle body, a dongle, and/or a mobile, general purpose, computing device, such as a mobile phone or tablet computer.

Tip assembly 1000 further comprises a printed circuit board (PCB) 1040. Image sensor(s) 1020 may be directly coupled with PCB 1040. However, light source(s) 1010 may be spaced apart from PCB 1040. More particularly, light source(s) 1010 may be positioned on a spacing mount 1017 that is configured to physically separate light source(s) 1010 from PCB 1040 and/or position light source(s) 1010 more closely to the distal end of the tip. In some preferred embodiments, light source(s) 1010 may be positioned so as to be flush, or at least substantially flush, with the distal end of the housing 1014 and/or the tip assembly 1000 itself. This may be useful in preventing a shadowing effect or otherwise creating a better image. Thus, in the depicted embodiment, light source/LED 1010 is positioned within a cavity 1019 (see FIG. 10B) formed within housing 1014. The perimeter of housing 1014 defining cavity 1019 may be flush with a distal end of tip assembly 1000.

Tip assembly 1000 further comprises a lens assembly 1011, cover glass 1035, and one or more fasteners, such as fasteners 1018 and 1023, which may be used to secure various components of assembly 1000 in place. One or more lenses or other optical components may be positioned within a lens cavity 1012 formed within lens assembly 1011 to provide desired focusing for image sensor 1020. Lens assembly 1011 may be positioned within a lens housing cavity 1015 formed within housing 1014. In some embodiments, threads, such as threads 613 in assembly 600, may be provided to allow lens assembly 1011 to be moved relative to housing 1014 to change the spacing between image sensor 1020 and the lens within lens assembly 1011.

Cover glass 1035 may be sealed to housing 1014 to prevent fluids from contacting lens assembly 1011 or otherwise entering tip assembly 1000, and may also serve a protective function. In the depicted embodiment, cover glass 1035 is specifically configured to cover the lens (in lens assembly 1011) and its associated image sensor 1020 without also covering light source/LED 1010. This may be useful to avoid having reflected light from the light source/LED 1010 enter the image sensor 1020 and blur the resulting image.

The portion of housing 1014 that surrounds light source/LED 1010 may be used to optically isolate light source/LED 1010 from lateral exposure of light to image sensor 1020. For example, as mentioned above, light source/LED 1010 is isolated from cover glass 1035 to prevent light from being reflected into image sensor 1020 prior to being reflected off of tissue. In addition, as also mentioned above, light source/LED is preferably set apart from PCB 1040 on which image sensor 1020 may be mounted, to further improve image quality. In some embodiments, light source/LED 1010 may be positioned distally relative to image sensor 1020 and also distally relative to cover glass 1035. However, in other embodiments, light source/LED 1010 may be positioned flush with, or even recessed/proximal with respect to, cover glass 1035.

Thus, the depicted embodiment comprises two transparent mediums physically separated from one another, one of which covers the lens and/or image sensor 1020 (cover glass 1035) and the other of which covers the light source/LED 1010. In the depicted embodiment, the transparent medium covering light source/LED 1010 may comprise an epoxy that encases the light source/LED 1010. However, other embodiments are contemplated in which a separate transparent cover is positioned distally of light source/LED 1010, such as at the distal end of cavity 1019 flush with the distal end of housing 1014. Still other embodiments are contemplated in which light source/LED 1010 is sealed adjacent to an exterior surface of assembly 1000 such that a transparent light source cover is not needed. However, it is preferred that whatever cover is used does not extend over both the light source and the lens/image sensor, as previously mentioned, to avoid reflection blurring.

Image sensor 1020 may comprise a CMOS sensor or any other image sensor available to one of ordinary skill in the art, and may be configured to capture images and/or video in a variety of different resolutions, including, but not limited to 720p, 720i, 1080p, 1080i, and other similar high resolution formats.

As mentioned above, light source/LED 1010 may be mounted to housing 1014. In preferred embodiments, light source/LED 1010 may be mounted flush, or at least substantially flush, with the end of housing 1014 (which may also coincide with the end of assembly 1000 in some embodiments) so as to minimize tunneling of light. However, in other embodiments, light source/LED 1010 may be recessed from, or may extend beyond, the distal end of housing 1014 and/or the distal end of assembly 1000.

In some embodiments, the light source/LED 1010 and image sensor 1020 may be coupled with the same PCB 1040. In such embodiments, it may be useful to still physically separate the light source/LED 1010 from the PCB 1040, as mentioned above. However, in other embodiments, a different PCB may be provided for the light source/LED 1010 and image sensor 1020. For example, in some embodiments, spacing mount 1017 may also, or alternatively, comprise a PCB such that light source/LED 1010 and image sensor 1020 are electrically coupled with distinct PCBs. In such embodiments, spacing mount 1017 may serve as both a PCB and as a means for spacing the light source/LED 1010 apart from the other PCB 1040 upon which the image sensor 1020 may be positioned.

One or more of the PCBs, such as spacing mount/PCB 1017 and/or PCB 1040, may comprise a component, such as flash memory component 1042 or other non-volatile memory component, that may be configured to record the duration and/or number of uses of the device. This feature may be used to prevent or at least inhibit uses of a disposable component (in some embodiments, the entire borescope device other than a dongle for image processing) of the device beyond a preconfigured number or time duration.

Thus, for example, in some embodiments, the memory component may be configured to store cycle on/offs associated with the device and may be configured to transmit a command upon detecting a threshold number of uses to cause the device to become disabled, or to otherwise limit use of the device. Similarly, in other embodiments, the memory component may be configured to track and/or record the duration of time during which the device is on and/or being operated. The device may be configured to receive a command upon detecting a threshold time duration of use to cause the device to become disabled, or to otherwise limit use of the device.

In some embodiments, the threshold may be a single use. In other words, some embodiments may be specifically configured to allow for use of the device in a single procedure, and may then preclude, or at least inhibit, attempts at further uses.

In alternative embodiments, the memory component may be located elsewhere within the tip assembly 1000, or elsewhere within the borescope device. In some embodiments, the tip assembly may comprise smart chips, electronic counters, or time-based lockouts to provide an indication of usage times and/or durations. Such data may then be stored in the tip assembly, such as on a flash memory component or other non-volatile memory component on a PCB within the tip assembly.

Steps of a method for detecting a threshold number and/or duration of use, and/or steps of a method for disabling or otherwise limiting use of the device upon detecting the threshold may be implemented using machine-readable instructions stored on a non-transitory, machine-readable media, which may be located in the tip/device or, alternatively, on the dongle or a general-purpose mobile computing device.

In some embodiments, the dongle may be configured to limit use of the borescope in response to receiving and/or detecting a particular condition, such as a use condition exceeding a threshold. Thus, in some embodiments, the dongle may be configured to query the borescope and, in response to detecting or determining that, for example, at least one of a threshold duration and a threshold number of uses of the borescope device has been exceeded disabling the borescope, providing an audible warning, providing a visible warning, and/or transmitting a warning signal to attempt to inhibit or prevent further use of the borescope.

In some embodiments, usage data may be stored on the dongle instead of, or in addition to, in the borescope device itself. Thus, the dongle may be configured to receive usage data, such as the number of hours, number of power cycles, time stamps, etc., from the borescope or, alternatively, may be configured to detect some or all of this data on its own. For example, in some embodiments, the dongle may be configured to detect a power up or power cycle and initiate a timer or clock. Upon detecting a power down or second power cycle, the dongle may be configured to stop the timer/clock. In this manner, data need not be stored on the borescope itself, which may limit cost, particularly for disposable medical borescope devices.

This usage data, whether generated at the borescope or the dongle, may simply be stored for record keeping or, alternatively, may be configured to result in one or more actions, as described above, such as upon detecting a threshold condition.

In some embodiments, other instructions, settings, or data may alternatively, or additionally, be stored on PCB 1040 and/or otherwise in tip assembly 1000. For example, in some embodiments, zoom settings, lighting settings, image processing settings, or other similar settings or data may be stored in non-transitory memory located on PCB 1040 and/or otherwise in tip assembly 1000. Such data may also, or alternatively, be stored on a dongle that may be configured to be detachably coupled with tip assembly 1000 such that tip assembly 1000 and/or one or more other components of a borescope may be disposed of after one use or a limited number of uses.

FIGS. 11A and 11B depict a handle body 1100 for a borescope system according to an alternative embodiment. Handle body 1100 comprises a distal end 1102, from which a borescope tube may extend. Handle body 1100 further comprises a proximal end 1104, from which one or more wires may extend. As described above, such wires may be coupled with a dongle and/or a mobile computing device in some embodiments.

A port 1106 at distal end 1102 may be configured to receive the borescope tube. In some embodiments, the borescope tube may be releasably coupled with port 1106. Alternatively, the borescope tube may be permanently affixed to handle body 1100 at port 1106. Similarly, at the proximal end 1104, another port 1108 may be provided through which one or more wires may extend for delivering imaging data to a dongle, computing device, and/or display.

Handle body 1100 further comprises a narrowed stem 1110 adjacent to the proximal end 1104, which may allow a user to confirm, by either tactile or visual inspection, that the handle body 1100 is in a desired rotational orientation during a procedure. Narrowed stem 1110 also partially defines a recess 1115 on the bottom surface of handle body 1100. Recess 1115 also provides the ability to confirm by either tactile or visual inspection that the handle body 1100 is in a desired rotational orientation during a procedure. In use, it is anticipated that a surgeon/user would hold handle body 1100 with one or more of the user's fingers, such as most typically the pinky and/or ring finger, resting within recess 1115, during use. Thus, recess 1115 and/or narrowed stem 1110 are additional examples of means for confirming a rotational orientation of a borescope handle.

In some embodiments, the dongle and/or the borescope, such as tip assembly 1000, may be used to store data that may be useful for regulatory record-keeping, incident reporting, or general record keeping. In other words, the dongle and/or borescope may be configured to act similar to a "black box" in the airline industry. More particularly, in some embodiments, usage data may be obtained from the medical borescope during a medical procedure and may be stored, either on the borescope device itself or on the dongle, to allow for later access in order to obtain information regarding usage of the medical borescope during the medical procedure. Such information may allow for regulatory agencies, courts, or the like to determine what took place and/or at what time during a particular procedure. Or such information may simply be used for internal company/hospital record keeping purposes. In some embodiments, the usage data may be correlated with other data, such as time data and or model/device identification data so that a better picture of one or more events and the devices used to perform a medical procedure may be obtained and stored. Providing model/device identification data may be particularly useful in connection with embodiments in which the dongle is used to store the black-box data, since the dongle may be removed and used with other borescopes while maintaining the link between the stored data and the device used to perform a particular procedure.

Such usage data may allow for recreation of certain aspects of a medical procedure. In some embodiments and implementations, the usage data may comprise one or more of, for example, a duration of a medical procedure, an image associated with a medical procedure, such as an image triggered by an unexpected event during the medical procedure, a time stamp associated with the medical procedure, a temperature measurement associated with the medical procedure, an orientation of the borescope, a location of the borescope, a velocity of the borescope, such as a peak velocity of the borescope during a medical procedure, and a power cycle counter associated with the medical borescope.

Alternatively, or additionally, parameter and/or calibration data may be stored on the dongle and/or borescope device and/or transmitted to the dongle and/or another device, either separately from or along with the usage data. For example, in some embodiments and implementations, model identification data, such as, for example, a serial number or a model number associated with the medical borescope, may be stored. In some such embodiments, the model identification data may be stored within the borescope device, such as within a memory component on the tip of the device, for example. Such data may then allow the dongle to query the borescope and to adjust an operational and/or control parameter in accordance with the particular borescope detected. In this manner, a single dongle may be used with a variety of different scopes. For example, the dongle may determine whether the scope is an HD scope or an SD scope, the size of the lens used on the scope, the type and/or number of lights, etc. This information may also be used to enable or disable certain features on the scope depending upon its functionality.

In some embodiments and implementations, usage data may only be used for the "black box" purposes referenced above. In other embodiments and implementations, only model identification data may be obtained and stored. Alternatively, usage data may be obtained and used for different purposes, either in addition to or as an alternative to the black box purposes. For example, usage data may be used to limit the duration and/or number of uses of the device, as discussed elsewhere herein. In some such embodiments, the usage data may be used to enforce/control the disposability of one or more portions of the borescope.

In some embodiments, certain data may be stored in the borescope and queried by and/or sent to the dongle for further controlling/limiting use of the device in this manner. For example, in some embodiments, a number of allowable uses, an allowable duration of use, and/or an allowed operational configuration may be stored within a memory component of the borescope and, upon coupling with a dongle, may be obtained by the dongle to enforce such control parameters. In some embodiments, upon detecting that a control parameter threshold has been exceeded, the dongle may be configured to disable or otherwise limit further use of the borescope device.

In some embodiments and implementations, calibration data may be stored on the borescope device and/or dongle. In certain preferred embodiments, such calibration data may be stored on the borescope device, such as on a memory component that may be located in a tip of the borescope device, and may be queried by and/or sent to the dongle. Other data that may operate in conjunction with such calibration data may be stored on the dongle. For example, in some embodiments, lens calibration data, such as correction parameters, may be stored on the borescope and/or dongle, such that the dongle can query the borescope for certain lens calibration data and apply appropriate corrections according to the lens data received from the borescope without having to query a centralized database. As another example of calibration data, white balance parameters may be stored on the borescope and/or dongle such that, if a particular LED has sufficient variation from part to part and/or if multiple LED manufacturers are used for a certain borescope or set of borescopes, the color spectral content of the LED for a particular scope may be stored on a memory component in the scope and, in some such embodiments, such data may be sent to the dongle for use in calibration of the borescope prior to a procedure.

Figure 12A:
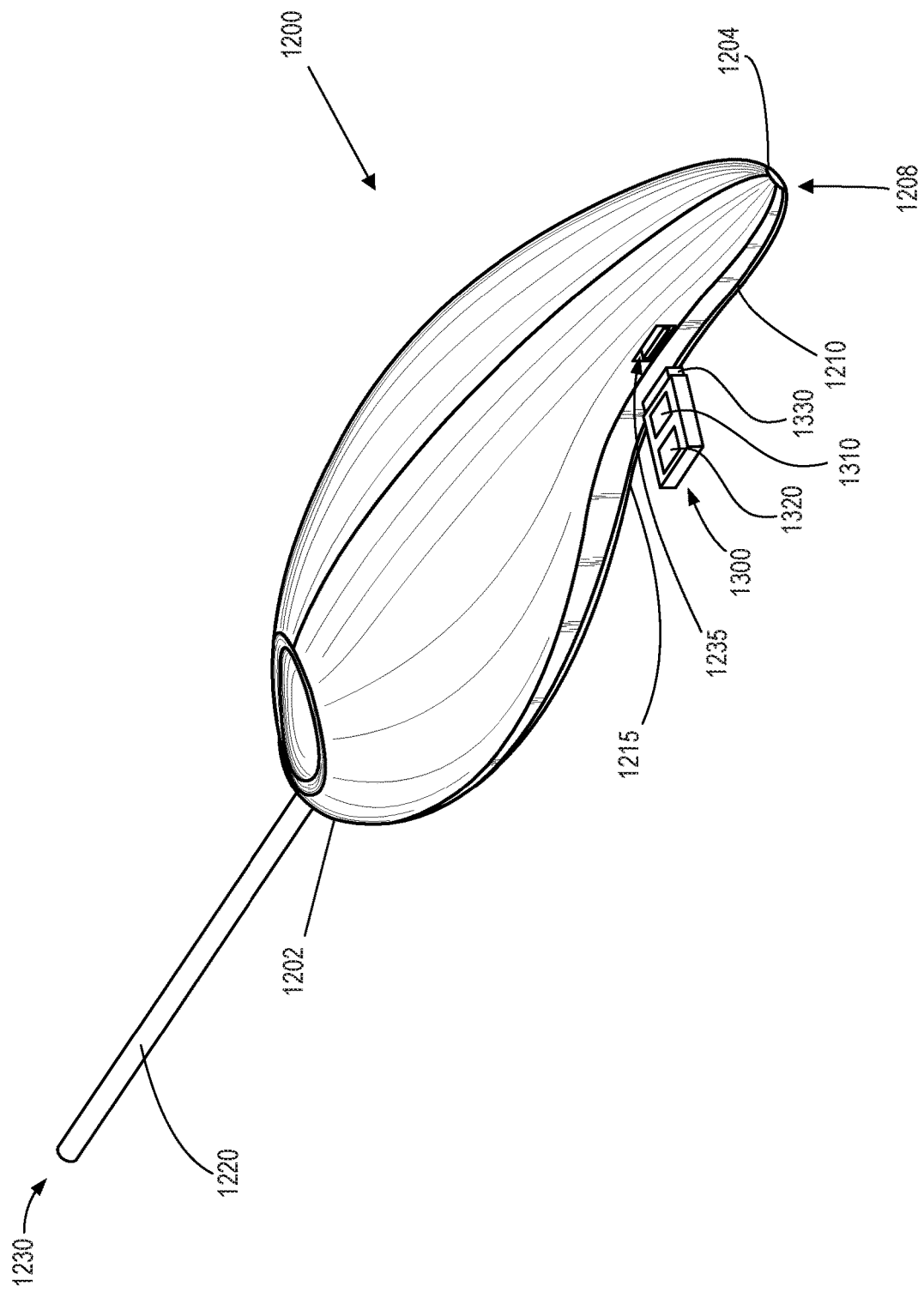
FIG. 12A is a perspective view of a borescope system according to another alternative embodiment.
Figure 12B:
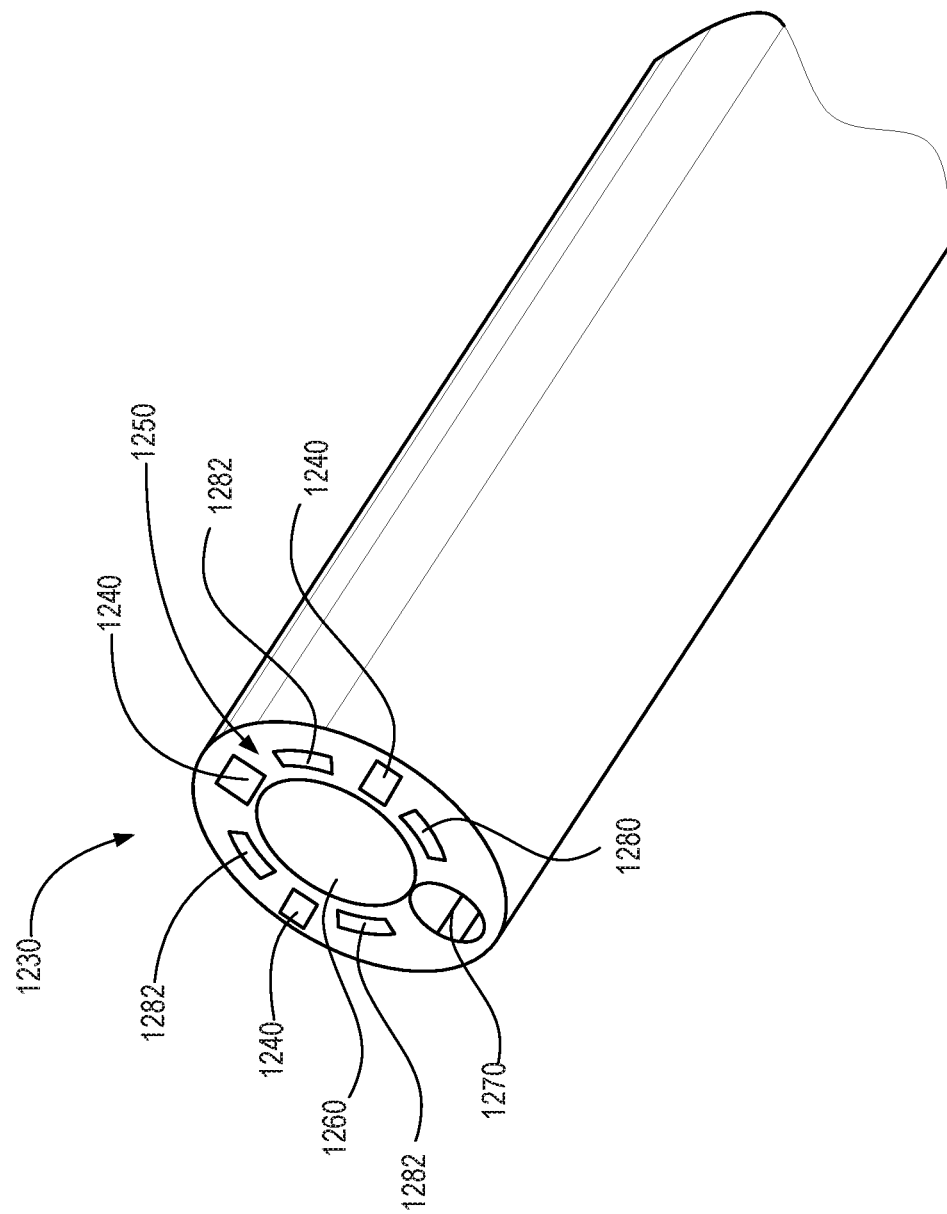
FIG. 12B is a close-up view of the tip of the borescope of the borescope system illustrated in FIG. 12A.

Another embodiment of a borescope 1200 is depicted in FIGS. 12A and 12B. Borescope 1200 comprises a handle having a distal end 1202, from which a borescope tube 1220 extends. In preferred embodiments, borescope tube 1220 comprises a non-conductive material, such as polycarbonate or polyether ether ketone (PEEK). This may provide several benefits, such as preventing arcing, which may contribute to the safety of the device. The inventors have also discovered that non-conductive tubes may provide desirable electromagnetic isolation, which may prevent or at least reduce electromagnetic interference (EMI) with signals generated within tube 1220. Providing a non-conductive tube portion may also simplify the configuration needed to provide EMI shielding.

Borescope 1200 further comprises a proximal end 1204. Rather than comprising wires that may be coupled to a dongle, borescope 1200 comprises a dongle 1300 that can be inserted directly into a port 1235 formed within the handle of borescope 1200. However, a port 1208 may still be formed at proximal end 1204 for other purposes if desired.

Dongle 1300 further comprises a memory element 1310, and a processor 1320, which, as discussed above, may be used to process image data from an image sensor in the borescope 1200, as discussed above. Dongle 1300 further comprises a data port 1330, which may be used to couple dongle 1300 with borescope 1200 and, in some embodiments, may also allow dongle 1300 to be coupled with another device, such as a general-purpose computer. In this manner, as discussed above, data obtained from borescope 1200, such as usage data, may be stored in memory element 1310 and ultimately transferred to another computer following a medical procedure.

The handle of borescope 1200 further comprises a narrowed stem 1210 adjacent to the proximal end 1204, which may allow a user to confirm, by either tactile or visual inspection, that the handle is in a desired rotational orientation during a procedure, as previously mentioned. Narrowed stem 1210 also partially defines a recess 1215 on the bottom surface of the handle body. Recess 1215 also provides the ability to confirm by either tactile or visual inspection that the handle body 1200 is in a desired rotational orientation during a procedure.

Borescope tube 1220 comprises a tip 1230. Tip 1230 and/or another component within borescope 1200 may comprise various additional functional elements. An example of such a combination of elements is depicted in FIG. 12B, which is a close-up view of tip 1230. Tip 1230 comprises three LEDs 1240 positioned in a circumferential manner relative to image sensor 1260. Tip 1230 may further comprise one or more through ports 1270 that may extend at least partially up the length of the borescope tube 1220 and/or the handle of borescope 1200. Tip 1230 may further comprise one or more lenses 1250, as previously discussed.

In order to facilitate one or more of the data storage/transmission aspects referenced above, tip 1230 may further comprise a memory element 1280 and one or more sensors 1282. Examples of sensors that may be useful in gathering data, such as usage data, include temperature sensors, pressure sensors, impedance sensors, gyroscopes, timers, clocks, etc. In some embodiments, one or more of sensors 1282 may comprise a second image sensor. Such image sensor may be used to capture images at select moments separate from the primary image sensor 1260. Data obtained during a surgical procedure from such sensor(s) may be stored in memory element 1280 and, ultimately, in some embodiments, may be sent to a similar memory element, such as memory element 1310, located within dongle 1300.

Figure 13:
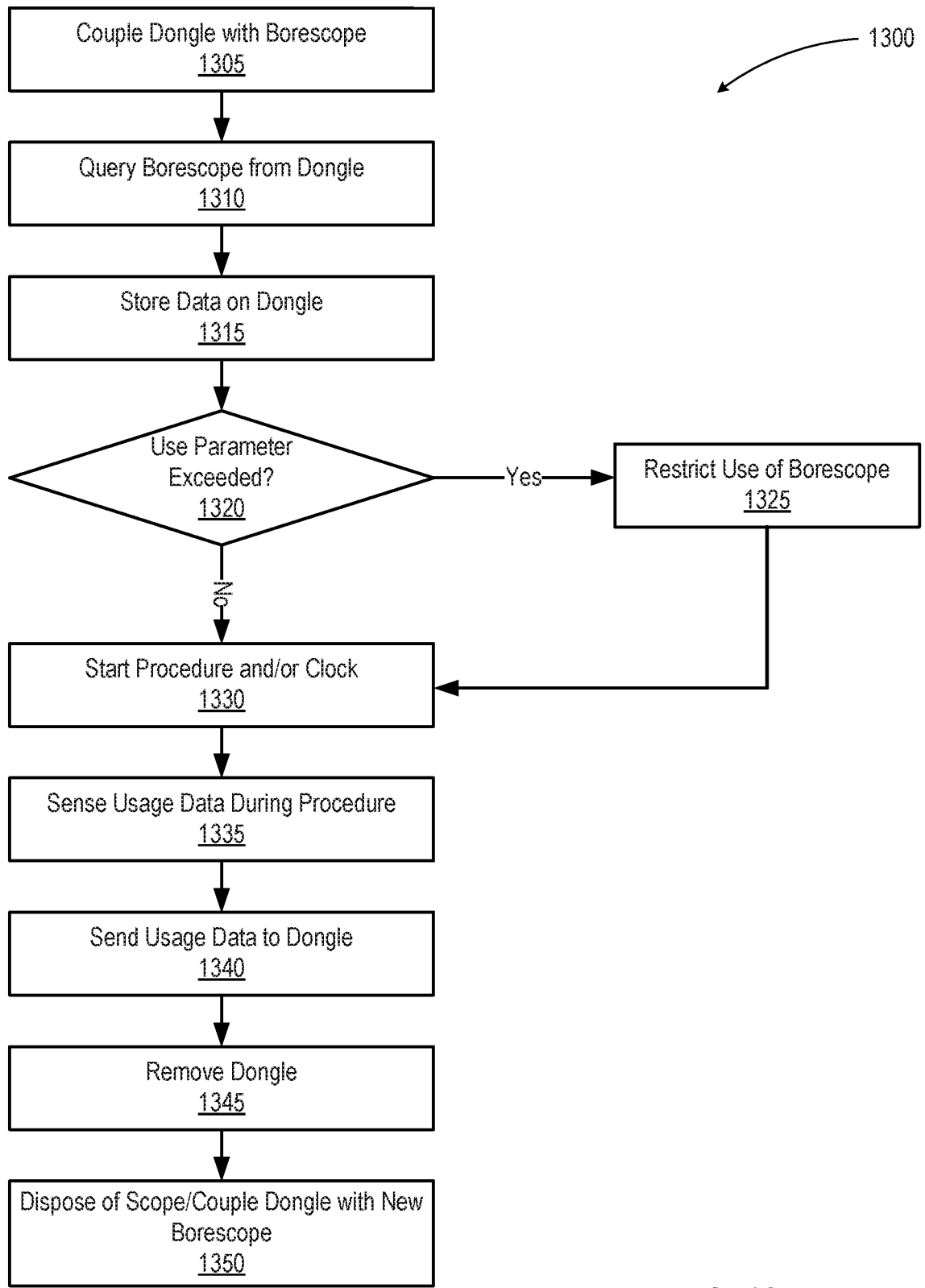
FIG. 13 is a flow chart illustrating an example of a method for use of a borescope system according to some implementations.

An example of a method 1300 for use of a borescope system comprising a borescope device and a dongle is illustrated in the flow chart of FIG. 13. Method 1300 begins with step 1305 at which a dongle may be coupled with a borescope. In some implementations, the dongle may be coupled with a disposable borescope. The borescope may then be queried by the dongle at step 1310. In some implementations, step 1310 may comprise querying the borescope for model identification data, such as a serial number and/or model identification. Alternatively, or additionally, calibration data may be obtained from the borescope. Alternatively, or additionally, usage parameters and/or prior usage data may be obtained at step 1310 so that the dongle may facilitate limiting unwanted use of the borescope. At step 1315, the data obtained from the borescope may be stored on the dongle for later use.

At step 1320, an inquiry may be made as to whether a use parameter has been exceeded. For example, as discussed above, in some implementations, a query may be made by the dongle as to whether the borescope has been used before, or whether the borescope has exceeded a predetermined threshold duration or number of uses. If so, further use of the borescope may be restricted at step 1325. For example, in some implementations, the dongle may disable one or more functions of the borescope at step 1325. If a use parameter has not been exceeded, process 1300 may proceed to step 1330, at which point a procedure may begin using the borescope. In some implementations, step 1330 may further comprise initiating a clock or counter to allow for tracking further use of the device.

Following step 1330, usage data may be sensed during the medical procedure at step 1335. For example, as mentioned above, one or more sensors located in the tip and/or elsewhere in the borescope may be used to track and/or record various aspects of the procedure for later recovery. In some implementations, process 1300 may return to step 1320 at various points throughout the procedure along with, or as an alternative to, having step 1320 precede a medical procedure. For example, in some embodiments, the dongle, or another element of the system, may track use of the borescope and/or periodically query such use to determine whether the use parameter is exceeded during a medical procedure along with sensing usage data during the procedure.

Usage data obtained during the procedure may be sent to the dongle at step 1340. This may occur as the data is gathered in step 1335 or may occur after the procedure has been completed. In alternative implementations, usage data may simply be stored within the tip or another location within the borescope device itself rather than on the dongle.

Following step 1340, the dongle may be removed at step 1345 to allow for storage of the data obtained during the procedure. In some implementations, one or more portions of the scope may then be disposed of and the dongle may be coupled and used with a new borescope at step 1350.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A medical borescope, comprising:
  a handle;
  a tube extending from the handle;
  an image sensor; and
  a data storage element configured to receive and store usage data regarding the medical borescope associated with a specific medical procedure performed using the medical borescope, wherein the usage data comprises at least one of a duration of a medical procedure, an image associated with a medical procedure, a time stamp associated with the medical procedure, a temperature measurement associated with the medical procedure, an orientation of the borescope during the medical procedure, a location of the borescope during the medical procedure, and a velocity of the borescope during the medical procedure, and wherein the medical borescope is further configured to store device identification data associated with the medical borescope to allow for recreation of at least one part of a specific medical procedure using the medical borescope.

2. The medical borescope of claim 1, further comprising a dongle comprising an image processor configured to receive image data from the image sensor, wherein the dongle is removably coupleable with the handle of the medical borescope such that the dongle can be coupled with a plurality of distinct medical borescopes.

3. The medical borescope of claim 2, wherein the data storage element is part of the dongle.

4. The medical borescope of claim 1, further comprising a tip assembly positioned at a distal end of the tube, wherein the tip assembly comprises the image sensor.

5. The medical borescope of claim 4, wherein the data storage element is part of the tip assembly.

6. The medical borescope of claim 1, wherein the tube comprises a non-conductive material.

7. The medical borescope of claim 6, wherein the tube is wholly defined by a non-conductive material.

8. The medical borescope of claim 1, further comprising at least one of a clock and a timer, and wherein the medical borescope is configured to correlate at least some of the usage data with time data using the at least one of a clock and a timer.

9. A medical borescope, comprising:
   a handle;
   a shaft extending from the handle;
   an image sensor positioned at a distal end of the handle;
   at least one sensor configured to obtain sensor data comprising at least one of temperature, pressure, velocity, and orientation of the medical borescope during a medical procedure; and
   a data storage element configured to receive and store usage data regarding the medical borescope associated with a specific medical procedure performed using the medical borescope using the at least one sensor, wherein the data storage element is further configured to store device identification data and link the device identification data with the usage data to allow for recreation of at least one aspect of a medical procedure.

10. The medical borescope of claim 9, wherein the usage data comprises at least one of a duration of the medical procedure, a time stamp associated with the medical procedure, a temperature measurement associated with the medical procedure, an orientation of the borescope during the medical procedure, a location of the borescope during the medical procedure, and a velocity of the borescope during the medical procedure.

11. The medical borescope of claim 9, further comprising at least one of a timer and a clock, wherein the medical borescope is configured to correlate at least a portion of the usage data with a time and/or date stamp using the at least one of a timer and a clock.

12. The medical borescope of claim 9, wherein the shaft comprises a tube.

13. The medical borescope of claim 9, wherein the shaft comprises a non-conductive material.

14. The medical borescope of claim 13, wherein the shaft wholly comprises a non-conductive material.

15. A method for obtaining and storing data during a medical procedure using a medical borescope for subsequent recreation of at least a portion of the medical procedure, the method comprising the steps of:
   taking images of a medical procedure using an image sensor of a medical borescope;
   storing usage data regarding the medical procedure performed using the medical borescope, wherein the usage data comprises at least one of a duration of a medical procedure, an image associated with an unexpected event of the medical procedure, a time stamp associated with the medical procedure, a temperature measurement associated with the medical procedure, an orientation of the borescope during the medical procedure, a location of the borescope during the medical procedure, and a velocity of the borescope during the medical procedure; and
   correlating the usage data with device identification data used to identify the medical borescope used to perform the medical procedure to allow for subsequent recreation of at least one aspect of the medical procedure.

16. The method of claim 15, further comprising:
   removably coupling a dongle with the medical borescope; and
   processing image data using an image processor on the dongle.

17. The method of claim 16, wherein the usage data is stored on the dongle.

18. The method of claim 17, wherein the medical borescope is disposable, and further comprising:
   removing the dongle from the medical borescope;
   retrieving the usage data from the dongle; and
   coupling the dongle with a second medical borescope.

19. The method of claim 15, further comprising storing at least one of a date stamp and a time stamp associated with at least a portion of the medical procedure.

20. The method of claim 19, further comprising correlating the at least one of a date stamp and a time stamp with the usage data to allow for ascertaining a time period of the medical procedure.

* * * * *